United States Patent [19]
Schrader et al.

[11] Patent Number: 6,149,936
[45] Date of Patent: Nov. 21, 2000

[54] DNA EXPRESSION VECTORS FOR THE USE IN THE GENE THERAPEUTIC TREATMENT OF VASCULAR DISORDERS

[75] Inventors: Jürgen Schrader; Axel Gödecke, both of Düsseldorf, Germany

[73] Assignee: Joseph Schrader, Dusseldorf, Germany

[21] Appl. No.: 09/123,624

[22] Filed: Jul. 28, 1998

Related U.S. Application Data

[63] Continuation of application No. 08/553,503, filed as application No. PCT/EP95/01202, Mar. 31, 1995, abandoned.

[30] Foreign Application Priority Data

Mar. 31, 1994 [DE] Germany .............................. 44 11 402

[51] Int. Cl.$^7$ ........................ A61K 3/127; A61K 31/7088
[52] U.S. Cl. .............................................. 424/450; 514/44
[58] Field of Search .......................... 435/320.1; 514/12, 514/44; 536/23.1, 23.2, 23.5; 424/450

[56] References Cited

U.S. PATENT DOCUMENTS

| | | | |
|---|---|---|---|
| 5,132,407 | 7/1992 | Stuehr et al. | 530/395 |
| 5,252,479 | 10/1993 | Srivastava | 435/235.1 |
| 5,328,470 | 7/1994 | Nable et al. | 604/101 |
| 5,428,070 | 6/1995 | Cooke et al. | 514/557 |
| 5,468,630 | 11/1995 | Billiar et al. | 435/189 |
| 5,658,565 | 8/1997 | Billiar et al. | 424/93.21 |
| 5,766,909 | 6/1998 | Xie et al. | 435/189 |

FOREIGN PATENT DOCUMENTS

| | | |
|---|---|---|
| 0546796 | 6/1993 | European Pat. Off. . |
| 0441119 | 8/1993 | European Pat. Off. . |
| WO92/07943 | 5/1992 | WIPO . |
| WO93/18156 | 9/1993 | WIPO . |
| WO94/12645 | 6/1994 | WIPO . |
| WO94/23038 | 10/1994 | WIPO . |
| WO94/24269 | 10/1994 | WIPO . |
| WO94/28721 | 12/1994 | WIPO . |
| WO95/27070 | 10/1995 | WIPO . |
| WO96/00006 | 1/1996 | WIPO . |
| WO98/02170 | 1/1998 | WIPO . |

OTHER PUBLICATIONS

Nature, vol. 333, Jun. 16, 1988, pp. 66–666.
Biochem, Biophys. Commun., vol. 153, No. 3, Jun. 30, 1988, pp. 1251–1256.
Gen. Pharmac, vol. 21, No. 5, 1990, pp. 575–587.
J. Clin, Invest., vol. 90, 1992, pp. 1168–1172.
J. Clin. Invest, vol. 90, 1992, pp. 1248–1253.
Biochem, Biophysc. Res. Communc., vol. 191, No. 1, Feb. 26, 1993, pp. 89–94.
Nunokawa et al., "Cloning of Inducible Nitric Ozide Synthase in Rat Vascular Smooth Muscle Cells", *BioChemical and Biophysical Research Communications*; vol. 191, No. 1, Feb. 26,1993, pp. 89–94.
Bucala, et al., "Advanced Glycosylation Products Quench Nitric Oxide and Mediate Defective Endothelium–Dependant Vasodilalation in Experimental Diabetes"1991 J. Clin. Invest. 87:432–438.
Charles et al.; "Cloning Characterization and Expression of a cDNA Encoding an Induable Nitric Oxide Synthase From the Human Chondrocyte" Proc. Nat'l Acad. Sci USA 1993; Dec. 1, 90(23): 11419–11423 (1993).
Charles et al.; "Cloning and Expresion of a Rat Neuronal Nitric Oxide Synthase Coding Sequence in a Bacluovirus/Insect Cell System" Biochemical and Biophysical Research Communications, vol. 196, No. 3, 1481–1489 (1993).
Chester et al., "Low Basal and Stimulated Release of Nitric Oxide in Antherosclerotic Epicardial Coronary Arteries" 1990, Lancet 336: 897–900.
Chin et al., "Inactivation of Endothelial Derived Relaxing Factor by Oxidized Lipoproteins" 1992, J. Clin. Invest. 89:10–18.
Clowes et al. "Kinetics of Cellular Proliferation After Arterial Injury" (1983) 327–333.
Draiper et al., "L–arginine–derived Nitric Oxide and the Cell–Mediated Immune Response" 1991 Res. Immunol. 142:53–602.
Förstermann et al. v Eurpoean Heart Journal (1993) 14 (Supp. I), "Isoforms of Nitric Oxide Synthase: Functions in the Cardiovascular System".
Feldman et al. "Site Specificity of Adernovirus—Medicated Gene Transfer by Hydrogelated Ballon" (Abstract) JACC Feb. 1994:1A–484A (p. 235A).
Geller et al., "Molecular Cloning And Expression of Inducible Nitric Oxide Synthase from Human Hepatocytes" 1993 PNAS 90: 3491–3495.
Geller et al.; "Should Surgeons Clone Genes" Archives of Surgery; American Medical Assocition vol. 128 pp. 1212–1220 (Nov. 1993).
Ignarro et al. "Endothelium–Derived Relaxing Factor Produced and Released from Artery and Vein in Nitric Oxide" 1987 PNAS 84: 9265–9269.
Janssens et al.; "Cloning and Expression of a cDNA Encoding Human Endothelium–Derived Relaxing Factor/Nitric Oxide Synthase" The Journal of Biological Chemistry; vol. 267, No. 21 Issue of Jul. 25 pp. 14319–14522 (1992).
Lange et al. Southwestern Internal Medicine Conference:Restenosis (Od. 1983) pp. 265–275.
Lloyd–Jones, M.D. et al.; "The Vascular Biology of Nitric Oxide and its Role In Atherogenesis" Annu. Rev. Med. 1996, 47:365–75.
Lowenstein et al.; "Cloned and expressed macrophage nitric oxide synthase contrasts with the brain enzyme" Proc. Nat'l Acad. Sci. USA; vol. 89, pp. 6711–6715, Aug. 1992.

(List continued on next page.)

*Primary Examiner*—Robert A. Schwartzman
*Attorney, Agent, or Firm*—Frommer Lawrence & Haug LLP

[57] ABSTRACT

A DNA expression vector is described which is characterized in that it comprises a DNA sequence that codes a protein which possesses the biological activity of nitrogen monoxide synthase (NOS) and eukaryotic regulation elements, wherein said eukaryotic regulation elements result in the expression of said DNA sequence in eukaryotic cells, as well as the use of the expression vector for treatment or prevention of vascular disorders.

18 Claims, 24 Drawing Sheets

OTHER PUBLICATIONS

Lyons et al., "Molecular Cloning and Functional Expression of an Inducible Nitric Oxide Synthase from a Murine Macrophage Cell Line" 1992 J. Biol. Chem 267:6370–6374.

Moncada, et al. 1991, Nitric Oxide: Physiology, Pathophysiology and Pharmacology Pharmaceuticals Reviews 43: 109–142.

Nabel et al. "Recombinant Gene Expression In Vivo within Endothelial Cells of the Arterial Wall" *Science* 244: 1342–1344 (1989).

Nabel et al. "Site–specific Gene Expression In Vivo by Direct Gene Transfer into the Arterial Wall" 1990 Science 249:1285–1288.

Nakane et al.; "Cloned Human Brain Nitric Oxide Synthase is Highly Expressed In Skeletal Muscle" FEBS Letters, vol. 316, No. 2, 175–180; Jan. 1993.

Nakanishi et al. Efficient Introduction of Contents of Liposomes into Cells Using Hr3 (Sendai Virus) (1985) 399–409.

Nunokawa and Tanaka, "Intererfon–Gamma Inhibits Proliferation of Rat Vascular Smooth Muscle Cells by Nitric Oxide Generation" 1992, Biochem Biophys. Res. Comm. 188: 409–415.

Nussler et al. "Stimulation of Nitric Oxide in Human Hepatocytes by Cytokines" 1992 Faseb. J., 6(5):A1834(#5200).

Nussler, et al. "Stimulation of the Nitric Oxide Synthase Pathway in Human Hepatocytes by Cytokines and Endotoxins" 1992, J. Exp. Med. 176:261–264.

Radomski et al., "The Anti–Aggregating Properties of Vascular Endothelium: Interactions Between Prostacyclin and Nitric Oxide" 1987 Br. J. Pharmac. 92: 639–646.

Sessa; "Molecular Cloning and Expression of a cDNA Encoding Endothelial Cell Nitric Oxide Synthase" The Journal of Biological Chemistry; vol. 267, No. 22, Issue of Aug. 5, pp. 15274–15276, 1992.

Steg et al. Local Delivery of Adenovirus for Percutaneous Arterial Gene Transfer (abstract) Supplement to Circulation, vol. 88, No. 4, Para 2 (Oct. 1993) p. I–660.

von der Leyen et al., "In Vivo Gene Transfer to Prevent Neointima Hyperplasia after Vascular Injury: Effect of Overexpression of Constitutive Nitric Oxide Synthase" 1994 Faseb. J. 8:A802(#4651).

von der Leyen et al., "Gene Therapy Inhibiting Vascular Lesion: In Vivo Transfer of Endothelial Cell Nitric Oxide Synthase Gene" pNAS USA 92 pp. 1137–1141 (Feb. 1995).

Werner–Felmayer et al, "Tetrahydrobiopterin–Dependent Formation of Nitrite and Nitrate Fibroblasts" 1990 J. Exp. Med. 172: 1599–1607.

Wilson et al., "Implantation of Vascular Grafts Lines with Genetically Modified Endothelial Cells" 1989, Science 244: 1344–1346.

Xie, et al. "Cloning and Characterization of Inducible Nitric Oxide Synthase from Mouse Macrophages" 1992 Science 256:225–228.

Zwiebel et al. "High–Level Recombinant Gene Expression in Rabbit Endothelial Cells Transduced by Retroviral Vectors" 1989, Science 243:220–222.

Fig. 1

```
GAGACTCTGG CCCCACGGGA CACAGTGTCA CTGGTTTGAA ACTTCTCAGC CACCTTGGTG      60

AAGGGACTGA GCTGTTAGAG ACACTTCTGA GGCTCCTCAC GCTTGGGTCT TGTTCACTCC     120

ACGGAGTAGC CTAGTCAACT GCAAGAGAAC GGAGAACGTT GGATTTGGAG CAGAAGTGCA     180

AAGTCTCAGA C ATG GCT TGC CCC TGG AAG TTT CTC TTC AAA GTC AAA TCC     230
             Met Ala Cys Pro Trp Lys Phe Leu Phe Lys Val Lys Ser
              1               5                      10
```

| | | | | | | | | | | | | | | |
|---|---|---|---|---|---|---|---|---|---|---|---|---|---|---|
| TAC | CAA | AGT | GAC | CTG | AAA | GAG | GAA | AAG | GAC | ATT | AAC | AAC | AAC GTG AAG | 278 |
| Tyr | Gln | Ser | Asp | Leu | Lys | Glu | Glu | Lys | Asp | Ile | Asn | Asn | Asn Val Lys | |
| | 15 | | | | 20 | | | | 25 | | | | | |
| AAA | ACC | CCT | TGT | GCT | GTT | CTC | AGC | CCA | ACA | ATA | CAA | GAT | GAC CCT AAG | 326 |
| Lys | Thr | Pro | Cys | Ala | Val | Leu | Ser | Pro | Thr | Ile | Gln | Asp | Asp Pro Lys | |
| 30 | | | | 35 | | | | 40 | | | | | 45 | |
| AGT | CAC | CAA | AAT | GGC | TCC | CCG | CAG | CTC | CTC | ACT | GGG | ACA | GCA CAG AAT | 374 |
| Ser | His | Gln | Asn | Gly | Ser | Pro | Gln | Leu | Leu | Thr | Gly | Thr | Ala Gln Asn | |
| | | | | 50 | | | | | 55 | | | | 60 | |
| GTT | CCA | GAA | TCC | CTG | GAC | AAG | CTG | CAT | GTG | ACA | TCG | ACC | CGT CCA CAG | 422 |
| Val | Pro | Glu | Ser | Leu | Asp | Lys | Leu | His | Val | Thr | Ser | Thr | Arg Pro Gln | |
| | | | 65 | | | | 70 | | | | | 75 | | |
| TAT | GTG | AGG | ATC | AAA | AAC | TGG | GGC | AGT | GGA | GAG | ATT | TTG | CAT GAC ACT | 470 |
| Tyr | Val | Arg | Ile | Lys | Asn | Trp | Gly | Ser | Gly | Glu | Ile | Leu | His Asp Thr | |
| | | 80 | | | | | 85 | | | | | 90 | | |
| CTT | CAC | CAC | AAG | GCC | ACA | TCG | GAT | TTC | ACT | TGC | AAG | TCC | AAG TCT TGC | 518 |
| Leu | His | His | Lys | Ala | Thr | Ser | Asp | Phe | Thr | Cys | Lys | Ser | Lys Ser Cys | |
| | 95 | | | | 100 | | | | | 105 | | | | |
| TTG | GGG | TCC | ATC | ATG | AAC | CCC | AAG | AGT | TTG | ACC | AGA | GGA | CCC AGA GAC | 566 |
| Leu | Gly | Ser | Ile | Met | Asn | Pro | Lys | Ser | Leu | Thr | Arg | Gly | Pro Arg Asp | |
| 110 | | | | | 115 | | | | | 120 | | | | 125 |
| AAG | CCT | ACC | CCT | CTG | GAG | GAG | CTC | CTG | CCT | CAT | GCC | ATT | GAG TTC ATC | 614 |
| Lys | Pro | Thr | Pro | Leu | Glu | Glu | Leu | Leu | Pro | His | Ala | Ile | Glu Phe Ile | |
| | | | | 130 | | | | | 135 | | | | | 140 |
| AAC | CAG | TAT | TAT | GGC | TCC | TTT | AAA | GAG | GCA | AAA | ATA | GAG | GAA CAT CTG | 662 |
| Asn | Gln | Tyr | Tyr | Gly | Ser | Phe | Lys | Glu | Ala | Lys | Ile | Glu | Glu His Leu | |
| | | | | 145 | | | | | 150 | | | | | 155 |
| GCC | AGG | CTG | GAA | GCT | GTA | ACA | AAG | GAA | ATA | GAA | ACA | ACA | GGA ACC TAC | 710 |
| Ala | Arg | Leu | Glu | Ala | Val | Thr | Lys | Glu | Ile | Glu | Thr | Thr | Gly Thr Tyr | |
| | | 160 | | | | | 165 | | | | | 170 | | |
| CAG | CTC | ACT | CTG | GAT | GAG | CTC | ATC | TTT | GCC | ACC | AAG | ATG | GCC TGG AGG | 758 |
| Gln | Leu | Thr | Leu | Asp | Glu | Leu | Ile | Phe | Ala | Thr | Lys | Met | Ala Trp Arg | |
| | 175 | | | | | 180 | | | | | 185 | | | |
| AAT | GCC | CCT | CGC | TGC | ATC | GGC | AGG | ATC | CAG | TGG | TCC | AAC | CTG CAG GTC | 806 |
| Asn | Ala | Pro | Arg | Cys | Ile | Gly | Arg | Ile | Gln | Trp | Ser | Asn | Leu Gln Val | |
| 190 | | | | | 195 | | | | | 200 | | | | 205 |

Fig. 1 continuation

```
TTT GAC GCT CGG AAC TGT AGC ACA GCA CAG GAA ATG TTT CAG CAC ATC        854
Phe Asp Ala Arg Asn Cys Ser Thr Ala Gln Glu Met Phe Gln His Ile
            210                 215                 220

TGC AGA CAC ATA CTT TAT GCC ACC AAC AAT GGC AAC ATC AGG TCG GCC        902
Cys Arg His Ile Leu Tyr Ala Thr Asn Asn Gly Asn Ile Arg Ser Ala
            225                 230                 235

ATC ACT GTG TTC CCC CAG CGG AGT GAC GGC AAA CAT GAC TTC AGG CTC        950
Ile Thr Val Phe Pro Gln Arg Ser Asp Gly Lys His Asp Phe Arg Leu
            240                 245                 250

TGG AAT TCA CAG CTC ATC CGG TAC GCT GGC TAC CAG ATG CCC GAT GGC        998
Trp Asn Ser Gln Leu Ile Arg Tyr Ala Gly Tyr Gln Met Pro Asp Gly
        255                 260                 265

ACC ATC AGA GGG GAT GCT GCC ACC TTG GAG TTC ACC CAG TTG TGC ATC       1046
Thr Ile Arg Gly Asp Ala Ala Thr Leu Glu Phe Thr Gln Leu Cys Ile
270                 275                 280                 285

GAC CTA GGC TGG AAG CCC CGC TAT GGC CGC TTT GAT GTG CTG CCT CTG       1094
Asp Leu Gly Trp Lys Pro Arg Tyr Gly Arg Phe Asp Val Leu Pro Leu
                290                 295                 300

GTC TTG CAA GCT GAT GGT CAA GAT CCA GAG GTC TTT GAA ATC CCT CCT       1142
Val Leu Gln Ala Asp Gly Gln Asp Pro Glu Val Phe Glu Ile Pro Pro
            305                 310                 315

GAT CTT GTG TTG GAG GTG ACC ATG GAG CAT CCC AAG TAC GAG TGG TTC       1190
Asp Leu Val Leu Glu Val Thr Met Glu His Pro Lys Tyr Glu Trp Phe
        320                 325                 330

CAG GAG CTC GGG TTG AAG TGG TAT GCA CTG CCT GCC GTG GCC AAC ATG       1238
Gln Glu Leu Gly Leu Lys Trp Tyr Ala Leu Pro Ala Val Ala Asn Met
    335                 340                 345

CTA CTG GAG GTG GGT GGC CTC GAA TTC CCA GCC TGC CCC TTC AAT GGT       1286
Leu Leu Glu Val Gly Gly Leu Glu Phe Pro Ala Cys Pro Phe Asn Gly
350                 355                 360                 365

TGG TAC ATG GGC ACC GAG ATT GGA GTT CGA GAC TTC TGT GAC ACA CAG       1334
Trp Tyr Met Gly Thr Glu Ile Gly Val Arg Asp Phe Cys Asp Thr Gln
                370                 375                 380

CGC TAC AAC ATC CTG GAG GAA GTG GGC CGA AGG ATG GGC TTG GAG ACC       1382
Arg Tyr Asn Ile Leu Glu Glu Val Gly Arg Arg Met Gly Leu Glu Thr
            385                 390                 395

CAC ACA CTG GCC TCC CTC TGG AAA GAC CGG GCT GTC ACG GAG ATC AAT       1430
His Thr Leu Ala Ser Leu Trp Lys Asp Arg Ala Val Thr Glu Ile Asn
        400                 405                 410

GTG GCT GTG CTC CAT AGT TTC CAG AAG CAG AAT GTG ACC ATC ATG GAC       1478
Val Ala Val Leu His Ser Phe Gln Lys Gln Asn Val Thr Ile Met Asp
    415                 420                 425

CAC CAC ACA GCC TCA GAG TCC TTC ATG AAG CAC ATG CAG AAT GAG TAC       1526
His His Thr Ala Ser Glu Ser Phe Met Lys His Met Gln Asn Glu Tyr
430                 435                 440                 445
```

Fig. 1 continuation

```
CGG GCC CGT GGA GGC TGC CCG GCA GAC TGG ATT TGG CTG GTC CCT CCA    1574
Arg Ala Arg Gly Gly Cys Pro Ala Asp Trp Ile Trp Leu Val Pro Pro
            450                 455                 460

GTG TCT GGG AGC ATC ACC CCT GTG TTC CAC CAG GAG ATG TTG AAC TAT    1622
Val Ser Gly Ser Ile Thr Pro Val Phe His Gln Glu Met Leu Asn Tyr
            465                 470                 475

GTC CTA TCT CCA TTC TAC TAC TAC CAG ATC GAG CCC TGG AAG ACC CAC    1670
Val Leu Ser Pro Phe Tyr Tyr Tyr Gln Ile Glu Pro Trp Lys Thr His
            480                 485                 490

ATC TGG CAG AAT GAG AAG CTG AGG CCC AGG AGG AGA GAG ATC CGA TTT    1718
Ile Trp Gln Asn Glu Lys Leu Arg Pro Arg Arg Arg Glu Ile Arg Phe
    495                 500                 505

AGA GTC TTG GTG AAA GTG GTG TTC TTT GCT TCC ATG CTA ATG CGA AAG    1766
Arg Val Leu Val Lys Val Val Phe Phe Ala Ser Met Leu Met Arg Lys
510                 515                 520                 525

GTC ATG GCT TCA CGG GTC AGA GCC ACA GTC CTC TTT GCT ACT GAG ACA    1814
Val Met Ala Ser Arg Val Arg Ala Thr Val Leu Phe Ala Thr Glu Thr
            530                 535                 540

GGG AAG TCT GAA GCA CTA GCC AGG GAC CTG GCC ACC TTG TTC AGC TAC    1862
Gly Lys Ser Glu Ala Leu Ala Arg Asp Leu Ala Thr Leu Phe Ser Tyr
            545                 550                 555

GCC TTC AAC ACC AAG GTT GTC TGC ATG GAC CAG TAT AAG GCA AGC ACC    1910
Ala Phe Asn Thr Lys Val Val Cys Met Asp Gln Tyr Lys Ala Ser Thr
            560                 565                 570

TTG GAA GAG GAG CAA CTA CTG CTG GTG GTG ACA AGC ACA TTT GGG AAT    1958
Leu Glu Glu Glu Gln Leu Leu Leu Val Val Thr Ser Thr Phe Gly Asn
    575                 580                 585

GGA GAC TGT CCC AGC AAT GGG CAG ACT CTG AAG AAA TCT CTG TTC ATG    2006
Gly Asp Cys Pro Ser Asn Gly Gln Thr Leu Lys Lys Ser Leu Phe Met
590                 595                 600                 605

CTT AGA GAA CTC AAC CAC ACC TTC AGG TAT GCT GTG TTT GGC CTT GGC    2054
Leu Arg Glu Leu Asn His Thr Phe Arg Tyr Ala Val Phe Gly Leu Gly
            610                 615                 620

TCC AGC ATG TAC CCT CAG TTC TGC GCC TTT GCT CAT GAC ATC GAC CAG    2102
Ser Ser Met Tyr Pro Gln Phe Cys Ala Phe Ala His Asp Ile Asp Gln
            625                 630                 635

AAG CTG TCC CAC CTG GGA GCC TCT CAG CTT GCC CCA ACA GGA GAA GGG    2150
Lys Leu Ser His Leu Gly Ala Ser Gln Leu Ala Pro Thr Gly Glu Gly
            640                 645                 650

GAC GAA CTC AGT GGG CAG GAG GAT GCC TTC CGC AGC TGG GCT GTA CAA    2198
Asp Glu Leu Ser Gly Gln Glu Asp Ala Phe Arg Ser Trp Ala Val Gln
            655                 660                 665

ACC TTC CGG GCA GCC TGT GAG ACC TTT GAT GTC CGA AGC AAA CAT CAC    2246
Thr Phe Arg Ala Ala Cys Glu Thr Phe Asp Val Arg Ser Lys His His
670                 675                 680                 685
```

Fig. 1 continuation

```
ATT CAG ATC CCG AAA CGC TTC ACT TCC AAT GCA ACA TGG GAG CCA CAG       2294
Ile Gln Ile Pro Lys Arg Phe Thr Ser Asn Ala Thr Trp Glu Pro Gln
            690                 695                 700

CAA TAT AGG CTC ATC CAG AGC CCG GAG CCT TTA GAC CTC AAC AGA GCC       2342
Gln Tyr Arg Leu Ile Gln Ser Pro Glu Pro Leu Asp Leu Asn Arg Ala
            705                 710                 715

CTC AGC AGC ATC CAT GCA AAG AAC GTG TTT ACC ATG AGG CTG AAA TCC       2390
Leu Ser Ser Ile His Ala Lys Asn Val Phe Thr Met Arg Leu Lys Ser
            720                 725                 730

CAG CAG AAT CTG CAG AGT GAA AAG TCC AGC CGC ACC ACC CTC CTC GTT       2438
Gln Gln Asn Leu Gln Ser Glu Lys Ser Ser Arg Thr Thr Leu Leu Val
            735                 740                 745

CAG CTC ACC TTC GAG GGC AGC CGA GGG CCC AGC TAC CTG CCT GGG GAA       2486
Gln Leu Thr Phe Glu Gly Ser Arg Gly Pro Ser Tyr Leu Pro Gly Glu
750                 755                 760                 765

CAC CTG GGG ATC TTC CCA GGC AAC CAG ACC GCC CTG GTG CAG GGA ATC       2534
His Leu Gly Ile Phe Pro Gly Asn Gln Thr Ala Leu Val Gln Gly Ile
            770                 775                 780

TTG GAG CGA GTT GTG GAT TGT CCT ACA CCA CAC CAA ACT GTG TGC CTG       2582
Leu Glu Arg Val Val Asp Cys Pro Thr Pro His Gln Thr Val Cys Leu
            785                 790                 795

GAG GTT CTG GAT GAG AGC GGC AGC TAC TGG GTC AAA GAC AAG AGG CTG       2630
Glu Val Leu Asp Glu Ser Gly Ser Tyr Trp Val Lys Asp Lys Arg Leu
            800                 805                 810

CCC CCC TGC TCA CTC AGC CAA GCC CTC ACC TAC TTC CTG GAC ATT ACG       2678
Pro Pro Cys Ser Leu Ser Gln Ala Leu Thr Tyr Phe Leu Asp Ile Thr
            815                 820                 825

ACC CCT CCC ACC CAG CTG CAG CTC CAC AAG CTG GCT CGC TTT GCC ACG       2726
Thr Pro Pro Thr Gln Leu Gln Leu His Lys Leu Ala Arg Phe Ala Thr
830                 835                 840                 845

GAC GAG ACG GAT AGG CAG AGA TTG GAG GCC TTG TGT CAG CCC TCA GAG       2774
Asp Glu Thr Asp Arg Gln Arg Leu Glu Ala Leu Cys Gln Pro Ser Glu
            850                 855                 860

TAC AAT GAC TGG AAG TTC AGC AAC AAC CCC ACG TTC CTG GAG GTG CTT       2822
Tyr Asn Asp Trp Lys Phe Ser Asn Asn Pro Thr Phe Leu Glu Val Leu
            865                 870                 875

GAA GAG TTC CCT TCC TTG CAT GTG CCC GCT GCC TTC CTG CTG TCG CAG       2870
Glu Glu Phe Pro Ser Leu His Val Pro Ala Ala Phe Leu Leu Ser Gln
            880                 885                 890

CTC CCT ATC TTG AAG CCC CGC TAC TAC TCC ATC AGC TCC TCC CAG GAC       2918
Leu Pro Ile Leu Lys Pro Arg Tyr Tyr Ser Ile Ser Ser Ser Gln Asp
            895                 900                 905

CAC ACC CCC TCG GAG GTT CAC CTC ACT GTG GCC GTG GTC ACC TAC CGC       2966
His Thr Pro Ser Glu Val His Leu Thr Val Ala Val Val Thr Tyr Arg
910                 915                 920                 925
```

Fig. 1 continuation

```
ACC CGA GAT GGT CAG GGT CCC CTG CAC CAT GGT GTC TGC AGC ACT TGG        3014
Thr Arg Asp Gly Gln Gly Pro Leu His His Gly Val Cys Ser Thr Trp
            930             935             940

ATC AGG AAC CTG AAG CCC CAG GAC CCA GTG CCC TGC TTT GTG CGA AGT        3062
Ile Arg Asn Leu Lys Pro Gln Asp Pro Val Pro Cys Phe Val Arg Ser
            945             950             955

GTC AGT GGC TTC CAG CTC CCT GAG GAC CCC TCC CAG CCT TGC ATC CTC        3110
Val Ser Gly Phe Gln Leu Pro Glu Asp Pro Ser Gln Pro Cys Ile Leu
            960             965             970

ATT GGG CCT GGT ACG GGC ATT GCT CCC TTC CGA AGT TTC TGG CAG CAG        3158
Ile Gly Pro Gly Thr Gly Ile Ala Pro Phe Arg Ser Phe Trp Gln Gln
            975             980             985

CGG CTC CAT GAC TCC CAG CAC AAA GGG CTC AAA GGA GGC CGC ATG AGC        3206
Arg Leu His Asp Ser Gln His Lys Gly Leu Lys Gly Gly Arg Met Ser
990             995             1000            1005

TTG GTG TTT GGG TGC CGG CAC CCG GAG GAG GAC CAC CTC TAT CAG GAA        3254
Leu Val Phe Gly Cys Arg His Pro Glu Glu Asp His Leu Tyr Gln Glu
            1010            1015            1020

GAA ATG CAG GAG ATG GTC CGC AAG AGA GTG CTG TTC CAG GTG CAC ACA        3302
Glu Met Gln Glu Met Val Arg Lys Arg Val Leu Phe Gln Val His Thr
            1025            1030            1035

GGC TAC TCC CGG CTG CCC GGC AAA CCC AAG GTC TAC GTT CAG GAC ATC        3350
Gly Tyr Ser Arg Leu Pro Gly Lys Pro Lys Val Tyr Val Gln Asp Ile
            1040            1045            1050

GTG CAA AAG CAG CTG GCC AAT GAG GTA CTC AGC GTG CTC CAC GGG GAG        3398
Val Gln Lys Gln Leu Ala Asn Glu Val Leu Ser Val Leu His Gly Glu
            1055            1060            1065

CAG GGC CAC CTC TAC ATT TGC GGA GAT GTG CGC ATG GCT CGG GAT GTG        3446
Gln Gly His Leu Tyr Ile Cys Gly Asp Val Arg Met Ala Arg Asp Val
1070            1075            1080            1085

GCT ACC ACA TTG AAG AAG CTG GTG GCC ACC AAG CTG AAC TTG AGC GAG        3494
Ala Thr Thr Leu Lys Lys Leu Val Ala Thr Lys Leu Asn Leu Ser Glu
            1090            1095            1100

GAG CAG GTG GAA GAC TAT TTC TTC CAG CTC AAG AGC CAG AAA CGT TAT        3542
Glu Gln Val Glu Asp Tyr Phe Phe Gln Leu Lys Ser Gln Lys Arg Tyr
            1105            1110            1115

CAT GAA GAT ATC TTC GGT GCA GTC TTT TCC TAT GGG GCA AAA AAG GGC        3590
His Glu Asp Ile Phe Gly Ala Val Phe Ser Tyr Gly Ala Lys Lys Gly
            1120            1125            1130

AGC GCC TTG GAG GAG CCC AAA GCC ACG AGG CTC TGACAGCCCA GAGTTCCAGC      3643
Ser Ala Leu Glu Glu Pro Lys Ala Thr Arg Leu
            1135            1140
```

Fig. 1 continuation

```
TTCTGGCACT GAGTAAAGAT AATGGTGAGG GGCTTGGGGA GACAGCGAAA TGCAATCCCC    3703

CCCAAGCCCC TCATGTCATT CCCCCCTCCT CCACCCTACC AAGTAGTATT GTATTATTGT    3763

GGACTACTAA ATCTCTCTCC TCTCCTCCCT CCCCTCTCTC CCTTTCCTCC CTTCTTCTCC    3823

ACTCCCCAGC TCCCTCCTTC TCCTTCTCCT CCTTTGCCTC TCACTCTTCC TTGGAGCTGA    3883

GAGCAGAGAA AAACTCAACC TCCTGACTGA AGCACTTTGG GTCACCACCA GGAGGCACCA    3943

TGCCGCCGCT CTAATACTTA GCTGCACTAT GTACAGATAT TTATACTTCA TATTTAAGAA    4003

AACAGATACT TTTGTCTACT CCCAATGATG GCTTGGGCCT TTCCTGTATA ATTCCTTGAT    4063

GAAAAATATT TATATAAAAT ACATTTTATT TTAATCAAAA AAAAAAA                  4110
```

Fig. 2

```
GAGCGGACGG GCTCATGATG CCTCAGATCT GATCCGCATC TAACAGGCTG GCAATGAAGA    60

TACCCAGAGA ATAGTTCACA TCTATCATGC GTCACTTCTA GACACAGCCA TCAGACGCAT   120

CTCCTCCCCT TTCTGCCTGA CCTTAGGACA CGTCCCACCG CCTCTCTTGA CGTCTGCCTG   180

GTCAACCATC ACTTCCTTAG AGAATAAGGA GAGAGGCGGA TGCAGGAAAT CATGCCACCG   240

ACGGGCCACC AGCCATGAGT GGGTGACGCT GAGCTGACGT CAAAGACAGA GAGGGCTGAA   300

GCCTTGTCAG CACCTGTCAC CCCGGCTCCT GCTCTCCGTG TAGCCTGAAG CCTGGATCCT   360

CCTGGTGAAA TCATCTTGGC CTGATAGCAT TGTGAGGTCT TCAGACAGGA CCCCTCGGAA   420
```

| | | | |
|---|---|---|---|
| GCTAGTTACC ATG GAG GAT CAC ATG TTC GGT GTT CAG CAA ATC CAG CCC<br>Met Glu Asp His Met Phe Gly Val Gln Gln Ile Gln Pro<br>1145           1150                1155 | | | 469 |
| AAT GTC ATT TCT GTT CGT CTC TTC AAG CGC AAA GTT GGG GGC CTG GGA<br>Asn Val Ile Ser Val Arg Leu Phe Lys Arg Lys Val Gly Gly Leu Gly<br>     1160                1165                1170 | | | 517 |
| TTT CTG GTG AAG GAG CGG GTC AGT AAG CCG CCC GTG ATC ATC TCT GAC<br>Phe Leu Val Lys Glu Arg Val Ser Lys Pro Pro Val Ile Ile Ser Asp<br>     1175                1180                1185 | | | 565 |
| CTG ATT CGT GGG GGC GCC GCA GAG CAG AGT GGC CTC ATC CAG GCC GGA<br>Leu Ile Arg Gly Gly Ala Ala Glu Gln Ser Gly Leu Ile Gln Ala Gly<br>1190                1195                1200                1205 | | | 613 |
| GAC ATC ATT CTT GCG GTC AAC GGC CGG CCC TTG GTG GAC CTG AGC TAT<br>Asp Ile Ile Leu Ala Val Asn Gly Arg Pro Leu Val Asp Leu Ser Tyr<br>           1210                1215                1220 | | | 661 |
| GAC AGC GCC CTG GAG GTA CTC AGA GGC ATT GCC TCT GAG ACC CAC GTG<br>Asp Ser Ala Leu Glu Val Leu Arg Gly Ile Ala Ser Glu Thr His Val<br>     1225                1230                1235 | | | 709 |
| GTC CTC ATT CTG AGG GGC CCT GAA GGT TTC ACC ACG CAC CTG GAG ACC<br>Val Leu Ile Leu Arg Gly Pro Glu Gly Phe Thr Thr His Leu Glu Thr<br>     1240                1245                1250 | | | 757 |
| ACC TTT ACA GGT GAT GGG ACC CCC AAG ACC ATC CGG GTG ACA CAG CCC<br>Thr Phe Thr Gly Asp Gly Thr Pro Lys Thr Ile Arg Val Thr Gln Pro<br>     1255                1260                1265 | | | 805 |
| CTG GGT CCC CCC ACC AAA GCC GTG GAT CTG TCC CAC CAG CCA CCG GCC<br>Leu Gly Pro Pro Thr Lys Ala Val Asp Leu Ser His Gln Pro Pro Ala<br>1270                1275                1280                1285 | | | 853 |
| GGC AAA GAA CAG CCC CTG GCA GTG GAT GGG GCC TCG GGT CCC GGG AAT<br>Gly Lys Glu Gln Pro Leu Ala Val Asp Gly Ala Ser Gly Pro Gly Asn<br>           1290                1295                1300 | | | 901 |
| GGG CCT CAG CAT GCC TAC GAT GAT GGG CAG GAG GCT GGC TCA CTC CCC<br>Gly Pro Gln His Ala Tyr Asp Asp Gly Gln Glu Ala Gly Ser Leu Pro<br>           1305                1310                1315 | | | 949 |

Fig. 2 continuation

```
CAT GCC AAC GGC TGG CCC CAG GCC CCC AGG CAG GAC CCC GCG AAG AAA        997
His Ala Asn Gly Trp Pro Gln Ala Pro Arg Gln Asp Pro Ala Lys Lys
        1320                1325                1330

GCA ACC AGA GTC AGC CTC CAA GGC AGA GGG GAG AAC AAT GAA CTG CTC        1045
Ala Thr Arg Val Ser Leu Gln Gly Arg Gly Glu Asn Asn Glu Leu Leu
        1335                1340                1345

AAG GAG ATA GAG CCT GTG CTG AGC CTT CTC ACC AGT GGG AGC AGA GGG        1093
Lys Glu Ile Glu Pro Val Leu Ser Leu Leu Thr Ser Gly Ser Arg Gly
1350                1355                1360                1365

GTC AAG GGA GGG GCA CCT GCC AAG GCA GAG ATG AAA GAT ATG GGA ATC        1141
Val Lys Gly Gly Ala Pro Ala Lys Ala Glu Met Lys Asp Met Gly Ile
                1370                1375                1380

CAG GTG GAC AGA GAT TTG GAC GGC AAG TCA CAC AAA CCT CTG CCC CTC        1189
Gln Val Asp Arg Asp Leu Asp Gly Lys Ser His Lys Pro Leu Pro Leu
        1385                1390                1395

GGC GTG GAG AAC GAC CGA GTC TTC AAT GAC CTA TGG GGG AAG GGC AAT        1237
Gly Val Glu Asn Asp Arg Val Phe Asn Asp Leu Trp Gly Lys Gly Asn
        1400                1405                1410

GTG CCT GTC GTC CTC AAC AAC CCA TAT TCA GAG AAG GAG CAG CCC CCC        1285
Val Pro Val Val Leu Asn Asn Pro Tyr Ser Glu Lys Glu Gln Pro Pro
        1415                1420                1425

ACC TCA GGA AAA CAG TCC CCC ACA AAG AAT GGC AGC CCC TCC AAG TGT        1333
Thr Ser Gly Lys Gln Ser Pro Thr Lys Asn Gly Ser Pro Ser Lys Cys
1430                1435                1440                1445

CCA CGC TTC CTC AAG GTC AAG AAC TGG GAG ACT GAG GTG GTT CTC ACT        1381
Pro Arg Phe Leu Lys Val Lys Asn Trp Glu Thr Glu Val Val Leu Thr
                1450                1455                1460

GAC ACC CTC CAC CTT AAG AGC ACA TTG GAA ACG GGA TGC ACT GAG TAC        1429
Asp Thr Leu His Leu Lys Ser Thr Leu Glu Thr Gly Cys Thr Glu Tyr
        1465                1470                1475

ATC TGC ATG GGC TCC ATC ATG CAT CCT TCT CAG CAT GCA AGG AGG CCT        1477
Ile Cys Met Gly Ser Ile Met His Pro Ser Gln His Ala Arg Arg Pro
        1480                1485                1490

GAA GAC GTC CGC ACA AAA GGA CAG CTC TTC CCT CTC GCC AAA GAG TTT        1525
Glu Asp Val Arg Thr Lys Gly Gln Leu Phe Pro Leu Ala Lys Glu Phe
        1495                1500                1505

ATT GAT CAA TAC TAT TCA TCA ATT AAA AGA TTT GGC TCC AAA GCC CAC        1573
Ile Asp Gln Tyr Tyr Ser Ser Ile Lys Arg Phe Gly Ser Lys Ala His
1510                1515                1520                1525

ATG GAA AGG CTG GAA GAG GTG AAC AAA GAG ATC GAC ACC ACT AGC ACT        1621
Met Glu Arg Leu Glu Glu Val Asn Lys Glu Ile Asp Thr Thr Ser Thr
                1530                1535                1540

TAC CAG CTC AAG GAC ACA GAG CTC ATC TAT GGG GCC AAG CAC GCC TGG        1669
Tyr Gln Leu Lys Asp Thr Glu Leu Ile Tyr Gly Ala Lys His Ala Trp
        1545                1550                1555
```

Fig. 2 continuation

```
CGG AAT GCC TCG CGC TGT GTG GGC AGG ATC CAG TGG TCC AAG CTG CAG         1717
Arg Asn Ala Ser Arg Cys Val Gly Arg Ile Gln Trp Ser Lys Leu Gln
        1560                1565                1570

GTA TTC GAT GCC CGT GAC TGC ACC ACG GCC CAC GGG ATG TTC AAC TAC         1765
Val Phe Asp Ala Arg Asp Cys Thr Thr Ala His Gly Met Phe Asn Tyr
1575                1580                1585

ATC TGT AAC CAT GTC AAG TAT GCC ACC AAC AAA GGG AAC CTC AGG TCT         1813
Ile Cys Asn His Val Lys Tyr Ala Thr Asn Lys Gly Asn Leu Arg Ser
1590                1595                1600                1605

GCC ATC ACC ATA TTC CCC CAG AGG ACA GAC GGC AAG CAC GAC TTC CGA         1861
Ala Ile Thr Ile Phe Pro Gln Arg Thr Asp Gly Lys His Asp Phe Arg
                1610                1615                1620

GTC TGG AAC TCC CAG CTC ATC CGC TAC GCT GGC TAC AAG CAC CGT GAC         1909
Val Trp Asn Ser Gln Leu Ile Arg Tyr Ala Gly Tyr Lys His Arg Asp
                1625                1630                1635

GGC TCC ACC CTG GGG GAC CCA GCC AAT GTG CAG TTC ACA GAG ATA TGC         1957
Gly Ser Thr Leu Gly Asp Pro Ala Asn Val Gln Phe Thr Glu Ile Cys
        1640                1645                1650

ATA CAG CAG GGC TGG AAA CCG CCT AGA GGC CGC TTC GAT GTC CTG CCG         2005
Ile Gln Gln Gly Trp Lys Pro Pro Arg Gly Arg Phe Asp Val Leu Pro
        1655                1660                1665

CTC CTG CTT CAG GCC AAC GGC AAT GAC CCT GAG CTC TTC CAG ATT CCT         2053
Leu Leu Leu Gln Ala Asn Gly Asn Asp Pro Glu Leu Phe Gln Ile Pro
1670                1675                1680                1685

CCA GAG CTG GTG TTG GAA CTT CCC ATC AGG CAC CCC AAG TTT GAG TGG         2101
Pro Glu Leu Val Leu Glu Leu Pro Ile Arg His Pro Lys Phe Glu Trp
                1690                1695                1700

TTC AAG GAC CTG GCG CTG AAG TGG TAC GGC CTC CCC GCC GTG TCC AAC         2149
Phe Lys Asp Leu Ala Leu Lys Trp Tyr Gly Leu Pro Ala Val Ser Asn
        1705                1710                1715

ATG CTC CTA GAG ATT GGC GGC CTG GAG TTC AGC GCC TGT CCC TTC AGT         2197
Met Leu Leu Glu Ile Gly Gly Leu Glu Phe Ser Ala Cys Pro Phe Ser
        1720                1725                1730

GGC TGG TAC ATG GGC ACA GAG ATT GGT GTC CGC GAC TAC TGT GAC AAC         2245
Gly Trp Tyr Met Gly Thr Glu Ile Gly Val Arg Asp Tyr Cys Asp Asn
        1735                1740                1745

TCC CGC TAC AAT ATC CTG GAG GAA GTG GCC AAG AAG ATG AAC TTA GAC         2293
Ser Arg Tyr Asn Ile Leu Glu Glu Val Ala Lys Lys Met Asn Leu Asp
1750                1755                1760                1765

ATG AGG AAG ACG TCC TCC CTG TGG AAG GAC CAG GCG CTG GTG GAG ATC         2341
Met Arg Lys Thr Ser Ser Leu Trp Lys Asp Gln Ala Leu Val Glu Ile
                1770                1775                1780

AAT ATC GCG GTT CTC TAT AGC TTC CAG AGT GAC AAA GTG ACC ATT GTT         2389
Asn Ile Ala Val Leu Tyr Ser Phe Gln Ser Asp Lys Val Thr Ile Val
                1785                1790                1795
```

Fig. 2 continuation

```
GAC CAT CAC TCC GCC ACC GAG TCC TTC ATT AAG CAC ATG GAG AAT GAG    2437
Asp His His Ser Ala Thr Glu Ser Phe Ile Lys His Met Glu Asn Glu
        1800                1805                1810

TAC CGC TGC CGG GGG GGC TGC CCT GCC GAC TGG GTG TGG ATC GTG CCC    2485
Tyr Arg Cys Arg Gly Gly Cys Pro Ala Asp Trp Val Trp Ile Val Pro
        1815                1820                1825

CCC ATG TCC GGA AGC ATC ACC CCT GTG TTC CAC CAG GAG ATG CTC AAC    2533
Pro Met Ser Gly Ser Ile Thr Pro Val Phe His Gln Glu Met Leu Asn
1830                1835                1840                1845

TAC CGG CTC ACC CCC TCC TTC GAA TAC CAG CCT GAT CCC TGG AAC ACG    2581
Tyr Arg Leu Thr Pro Ser Phe Glu Tyr Gln Pro Asp Pro Trp Asn Thr
                1850                1855                1860

CAT GTC TGG AAA GGC ACC AAC GGG ACC CCC ACA AAG CGG CGA GCC ATC    2629
His Val Trp Lys Gly Thr Asn Gly Thr Pro Thr Lys Arg Arg Ala Ile
            1865                1870                1875

GGC TTC AAG AAG CTA GCA GAA GCT GTC AAG TTC TCG GCC AAG CTG ATG    2677
Gly Phe Lys Lys Leu Ala Glu Ala Val Lys Phe Ser Ala Lys Leu Met
        1880                1885                1890

GGG CAG GCT ATG GCC AAG AGG GTG AAA GCG ACC ATC CTC TAT GCC ACA    2725
Gly Gln Ala Met Ala Lys Arg Val Lys Ala Thr Ile Leu Tyr Ala Thr
1895                1900                1905

GAG ACA GGC AAA TCG CAA GCT TAT GCC AAG ACC TTG TGT GAG ATC TTC    2773
Glu Thr Gly Lys Ser Gln Ala Tyr Ala Lys Thr Leu Cys Glu Ile Phe
1910                1915                1920                1925

AAA CAC GCC TTT GAT GCC AAG GTG ATG TCC ATG GAA GAA TAT GAC ATT    2821
Lys His Ala Phe Asp Ala Lys Val Met Ser Met Glu Glu Tyr Asp Ile
                1930                1935                1940

GTG CAC CTG GAA CAT GAA ACT CTG GTC CTT GTG GTC ACC AGC ACC TTT    2869
Val His Leu Glu His Glu Thr Leu Val Leu Val Val Thr Ser Thr Phe
            1945                1950                1955

GGC AAT GGA GAT CCC CCT GAG AAT GGG GAG AAA TTC GGC TGT GCT TTG    2917
Gly Asn Gly Asp Pro Pro Glu Asn Gly Glu Lys Phe Gly Cys Ala Leu
        1960                1965                1970

ATG GAA ATG AGG CAC CCC AAC TCT GTG CAG GAA GAA AGG AAG AGC TAC    2965
Met Glu Met Arg His Pro Asn Ser Val Gln Glu Glu Arg Lys Ser Tyr
    1975                1980                1985

AAG GTC CGA TTC AAC AGC GTC TCC TCC TAC TCT GAC TCC CAA AAA TCA    3013
Lys Val Arg Phe Asn Ser Val Ser Ser Tyr Ser Asp Ser Gln Lys Ser
1990                1995                2000                2005

TCA GGC GAT GGG CCC GAC CTC AGA GAC AAC TTT GAG AGT GCT GGA CCC    3061
Ser Gly Asp Gly Pro Asp Leu Arg Asp Asn Phe Glu Ser Ala Gly Pro
            2010                2015                2020

CTG GCC AAT GTG AGG TTC TCA GTT TTT GGC CTC GGC TCA CGA GCA TAC    3109
Leu Ala Asn Val Arg Phe Ser Val Phe Gly Leu Gly Ser Arg Ala Tyr
        2025                2030                2035
```

Fig. 2 continuation

```
CCT CAC TTT TGC GCC TTC GGA CAC GCT GTG GAC ACC CTC CTG GAA GAA       3157
Pro His Phe Cys Ala Phe Gly His Ala Val Asp Thr Leu Leu Glu Glu
    2040                2045                2050

CTG GGA GGG GAG AGG ATC CTG AAG ATG AGG GAA GGG GAT GAG CTC TGT       3205
Leu Gly Gly Glu Arg Ile Leu Lys Met Arg Glu Gly Asp Glu Leu Cys
    2055                2060                2065

GGG CAG GAA GAG GCT TTC AGG ACC TGG GCC AAG AAG GTC TTC AAG GCA       3253
Gly Gln Glu Glu Ala Phe Arg Thr Trp Ala Lys Lys Val Phe Lys Ala
2070                2075                2080                2085

GCC TGT GAT GTC TTC TGT GTG GGA GAT GAT GTC AAC ATT GAA AAG GCC       3301
Ala Cys Asp Val Phe Cys Val Gly Asp Asp Val Asn Ile Glu Lys Ala
                2090                2095                2100

AAC AAT TCC CTC ATC AGC AAT GAT CGC AGC TGG AAG AGA AAC AAG TTC       3349
Asn Asn Ser Leu Ile Ser Asn Asp Arg Ser Trp Lys Arg Asn Lys Phe
                2105                2110                2115

CGC CTC ACC TTT GTG GCC GAA GCT CCA GAA CTC ACA CAA GGT CTA TCC       3397
Arg Leu Thr Phe Val Ala Glu Ala Pro Glu Leu Thr Gln Gly Leu Ser
                2120                2125                2130

AAT GTC CAC AAA AAG CGA GTC TCA GCT GCC CGG CTC CTT AGC CGT CAA       3445
Asn Val His Lys Lys Arg Val Ser Ala Ala Arg Leu Leu Ser Arg Gln
    2135                2140                2145

AAC CTC CAG AGC CCT AAA TCC AGT CGG TCA ACT ATC TTC GTG CGT CTC       3493
Asn Leu Gln Ser Pro Lys Ser Ser Arg Ser Thr Ile Phe Val Arg Leu
2150                2155                2160                2165

CAC ACC AAC GGG AGC CAG GAG CTG CAG TAC CAG CCT GGG GAC CAC CTG       3541
His Thr Asn Gly Ser Gln Glu Leu Gln Tyr Gln Pro Gly Asp His Leu
                2170                2175                2180

GGT GTC TTC CCT GGC AAC CAC GAG GAC CTC GTG AAT GCC CTG ATC GAG       3589
Gly Val Phe Pro Gly Asn His Glu Asp Leu Val Asn Ala Leu Ile Glu
                2185                2190                2195

CGG CTG GAG GAC GCG CCG CCT GTC AAC CAG ATG GTG AAA GTG GAA CTG       3637
Arg Leu Glu Asp Ala Pro Pro Val Asn Gln Met Val Lys Val Glu Leu
    2200                2205                2210

CTG GAG GAG CGG AAC ACG GCT TTA GGT GTC ATC AGT AAC TGG ACA GAC       3685
Leu Glu Glu Arg Asn Thr Ala Leu Gly Val Ile Ser Asn Trp Thr Asp
    2215                2220                2225

GAG CTC CGC CTC CCG CCC TGC ACC ATC TTC CAG GCC TTC AAG TAC TAC       3733
Glu Leu Arg Leu Pro Pro Cys Thr Ile Phe Gln Ala Phe Lys Tyr Tyr
2230                2235                2240                2245

CTG GAC ATC ACC ACG CCA CCA ACG CCT CTG CAG CTG CAG CAG TTT GCC       3781
Leu Asp Ile Thr Thr Pro Pro Thr Pro Leu Gln Leu Gln Gln Phe Ala
                2250                2255                2260

TCC CTA GCT ACC AGC GAG AAG GAG AAG CAG CGT CTG CTG GTC CTC AGC       3829
Ser Leu Ala Thr Ser Glu Lys Glu Lys Gln Arg Leu Leu Val Leu Ser
                2265                2270                2275
```

Fig. 2 continuation

```
AAG GGT TTG CAG GAG TAC GAG GAA TGG AAA TGG GGC AAG AAC CCC ACC        3877
Lys Gly Leu Gln Glu Tyr Glu Glu Trp Lys Trp Gly Lys Asn Pro Thr
        2280            2285            2290

ATC GTG GAG GTG CTG GAG GAG TTC CCA TCT ATC CAG ATG CCG GCC ACC        3925
Ile Val Glu Val Leu Glu Glu Phe Pro Ser Ile Gln Met Pro Ala Thr
2295            2300            2305

CTG CTC CTG ACC CAG CTG TCC CTG CTG CAG CCC CGC TAC TAT TCC ATC        3973
Leu Leu Leu Thr Gln Leu Ser Leu Leu Gln Pro Arg Tyr Tyr Ser Ile
2310            2315            2320            2325

AGC TCC TCC CCA GAC ATG TAC CCT GAT GAA GTG CAC CTC ACT GTG GCC        4021
Ser Ser Ser Pro Asp Met Tyr Pro Asp Glu Val His Leu Thr Val Ala
            2330            2335            2340

ATC GTT TCC TAC CGC ACT CGA GAT GGA GAA GGA CCA ATT CAC CAC GGC        4069
Ile Val Ser Tyr Arg Thr Arg Asp Gly Glu Gly Pro Ile His His Gly
        2345            2350            2355

GTA TGC TCC TCC TGG CTC AAC CGG ATA CAG GCT GAC GAA CTG GTC CCC        4117
Val Cys Ser Ser Trp Leu Asn Arg Ile Gln Ala Asp Glu Leu Val Pro
        2360            2365            2370

TGT TTC GTG AGA GGA GCA CCC AGC TTC CAC CTG CCC CGG AAC CCC CAA        4165
Cys Phe Val Arg Gly Ala Pro Ser Phe His Leu Pro Arg Asn Pro Gln
        2375            2380            2385

GTC CCC TGC ATC CTC GTT GGA CCA GGC ACC GGC ATT GCC CCT TTC CGA        4213
Val Pro Cys Ile Leu Val Gly Pro Gly Thr Gly Ile Ala Pro Phe Arg
2390            2395            2400            2405

AGC TTC TGG CAA CAG CGG CAA TTT GAT ATC CAA CAC AAA GGA ATG AAC        4261
Ser Phe Trp Gln Gln Arg Gln Phe Asp Ile Gln His Lys Gly Met Asn
            2410            2415            2420

CCC TGC CCC ATG GTC CTG GTC TTC GGG TGC CGG CAA TCC AAG ATA GAT        4309
Pro Cys Pro Met Val Leu Val Phe Gly Cys Arg Gln Ser Lys Ile Asp
        2425            2430            2435

CAT ATC TAC AGG GAA GAG ACC CTG CAG GCC AAG AAC AAG GGG GTC TTC        4357
His Ile Tyr Arg Glu Glu Thr Leu Gln Ala Lys Asn Lys Gly Val Phe
        2440            2445            2450

AGA GAG CTG TAC ACG GCT TAC TCC CGG GAG CCA GAC AAA CCA AAG AAG        4405
Arg Glu Leu Tyr Thr Ala Tyr Ser Arg Glu Pro Asp Lys Pro Lys Lys
        2455            2460            2465

TAC GTG CAG GAC ATC CTG CAG GAG CAG CTG GCG GAG TCT GTG TAC CGA        4453
Tyr Val Gln Asp Ile Leu Gln Glu Gln Leu Ala Glu Ser Val Tyr Arg
2470            2475            2480            2485

GCC CTG AAG GAG CAA GGG GGC CAC ATA TAC GTC TGT GGG GAC GTC ACC        4501
Ala Leu Lys Glu Gln Gly Gly His Ile Tyr Val Cys Gly Asp Val Thr
            2490            2495            2500

ATG GCT GCT GAT GTC CTC AAA GCC ATC CAG CGC ATC ATG ACC CAG CAG        4549
Met Ala Ala Asp Val Leu Lys Ala Ile Gln Arg Ile Met Thr Gln Gln
            2505            2510            2515
```

Fig. 2 continuation

```
GGG AAG CTC TCG GCA GAG GAC GCC GGC GTA TTC ATC AGC CGG ATG AGG           4597
Gly Lys Leu Ser Ala Glu Asp Ala Gly Val Phe Ile Ser Arg Met Arg
        2520                2525                2530

GAT GAC AAC CGA TAC CAT GAG GAT ATT TTT GGA GTC ACC CTG CGA ACG           4645
Asp Asp Asn Arg Tyr His Glu Asp Ile Phe Gly Val Thr Leu Arg Thr
        2535                2540                2545

ATC GAA GTG ACC AAC CGC CTT AGA TCT GAG TCC ATT GCC TTC ATT GAA           4693
Ile Glu Val Thr Asn Arg Leu Arg Ser Glu Ser Ile Ala Phe Ile Glu
2550                2555                2560                2565

GAG AGC AAA AAA GAC ACC GAT GAG GTT TTC AGC TCC TAACTGGACC                4739
Glu Ser Lys Lys Asp Thr Asp Glu Val Phe Ser Ser
                2570                2575

CTCTTGCCCA GCCGGCTGCA AGTTTGTAAG CGCGGGACAG A                             4780
```

Fig. 3

```
GAATTCGGCA CGAGGAGCCA CAGAGCAGAC GGAGGCCGCC CGTCCGGCCC CAGCGAC                    57

ATG GGC AAC TTG AAG AGT GTG GGC CAG GAG CCC GGG CCC CCC TGC GGC                  105
Met Gly Asn Leu Lys Ser Val Gly Gln Glu Pro Gly Pro Pro Cys Gly
    1435            1440            1445

CTG GGG CTG GGG CTG GGC CTC GGG CTA TGC GGC AAG CAG GGC CCA GCC                  153
Leu Gly Leu Gly Leu Gly Leu Gly Leu Cys Gly Lys Gln Gly Pro Ala
1450            1455            1460            1465

TCC CCG GCA CCT GAG CCC AGC CGG GCC CCC GCA CCC GCC ACC CCG CAC                  201
Ser Pro Ala Pro Glu Pro Ser Arg Ala Pro Ala Pro Ala Thr Pro His
                1470            1475            1480

GCG CCA GAC CAC AGC CCA GCT CCC AAC AGC CCC ACG CTG ACC CGG CCT                  249
Ala Pro Asp His Ser Pro Ala Pro Asn Ser Pro Thr Leu Thr Arg Pro
            1485            1490            1495

CCG GAG GGG CCC AAG TTC CCT CGC GTG AAG AAC TGG GAG CTG GGG AGC                  297
Pro Glu Gly Pro Lys Phe Pro Arg Val Lys Asn Trp Glu Leu Gly Ser
        1500            1505            1510

ATC ACC TAC GAC ACT CTG TGC GCG CAG TCC CAA CAG GAC GGG CCC TGC                  345
Ile Thr Tyr Asp Thr Leu Cys Ala Gln Ser Gln Gln Asp Gly Pro Cys
    1515            1520            1525

ACT CCC AGG CGC TGC CTG GGC TCC CTG GTG TTG CCC CGG AAA CTG CAG                  393
Thr Pro Arg Arg Cys Leu Gly Ser Leu Val Leu Pro Arg Lys Leu Gln
1530            1535            1540            1545

ACC CGG CCC TCC CCG GGA CCT CCA CCC GCT GAG CAG CTG CTG AGC CAG                  441
Thr Arg Pro Ser Pro Gly Pro Pro Pro Ala Glu Gln Leu Leu Ser Gln
                1550            1555            1560

GCC AGG GAC TTC ATC AAC CAG TAC TAC AGC TCC ATC AAG AGG AGC GGC                  489
Ala Arg Asp Phe Ile Asn Gln Tyr Tyr Ser Ser Ile Lys Arg Ser Gly
            1565            1570            1575

TCC CAG GCT CAC GAG GAG CGG CTT CAG GAG GTG GAG GCC GAG GTG GCA                  537
Ser Gln Ala His Glu Glu Arg Leu Gln Glu Val Glu Ala Glu Val Ala
        1580            1585            1590

TCC ACG GGC ACC ATC CAC CTC CGA GAG AGT GAG CTG GTG TTC GGG GCC                  585
Ser Thr Gly Thr Ile His Leu Arg Glu Ser Glu Leu Val Phe Gly Ala
    1595            1600            1605

AAG CAG GCC TGG CGC AAT GCA CCC CGC TGC GTG GGC CGC ATC CAG TGG                  633
Lys Gln Ala Trp Arg Asn Ala Pro Arg Cys Val Gly Arg Ile Gln Trp
1610            1615            1620            1625

GGG AAG CTG CAG GTG TTT GAT GCC CGG GAC TGC AGC TCA GCA CAG GAG                  681
Gly Lys Leu Gln Val Phe Asp Ala Arg Asp Cys Ser Ser Ala Gln Glu
                1630            1635            1640

ATG TTC ACC TAC ATC TGC AAC CAC ATC AAG TAC GCC ACC AAC CGC GGC                  729
Met Phe Thr Tyr Ile Cys Asn His Ile Lys Tyr Ala Thr Asn Arg Gly
            1645            1650            1655
```

Fig. 3 continuation

```
AAC CTT CGC TCG GCC ATC ACA GTG TTC CCG CAG CGC GCC CCG GGC CGC       777
Asn Leu Arg Ser Ala Ile Thr Val Phe Pro Gln Arg Ala Pro Gly Arg
    1660            1665            1670

GGA GAC TTC CGG ATC TGG AAC AGC CAG CTG GTG CGC TAC GCA GGC TAC       825
Gly Asp Phe Arg Ile Trp Asn Ser Gln Leu Val Arg Tyr Ala Gly Tyr
    1675            1680            1685

AGA CAG CAG GAT GGC TCT GTG CGT GGG GAC CCA GCC AAC GTG GAG ATC       873
Arg Gln Gln Asp Gly Ser Val Arg Gly Asp Pro Ala Asn Val Glu Ile
1690            1695            1700            1705

ACG GAG CTC TGC ATC CAG CAC GGC TGG ACC CCC GGA AAC GGC CGC TTC       921
Thr Glu Leu Cys Ile Gln His Gly Trp Thr Pro Gly Asn Gly Arg Phe
                1710            1715            1720

GAC GTG CTG CCC CTG CTC CAG GCC CCA GAC GAG GCT CCA GAG CTC           969
Asp Val Leu Pro Leu Leu Leu Gln Ala Pro Asp Glu Ala Pro Glu Leu
            1725            1730            1735

TTT GTT CTG CCC CCC GAG CTG GTC CTT GAA GTG CCC CTA GGA GCA CCC      1017
Phe Val Leu Pro Pro Glu Leu Val Leu Glu Val Pro Leu Gly Ala Pro
        1740            1745            1750

CAC ACT GGA GTG GTT CGC GGC CCT GGG CTG CGA TGG TAT GCC CTC CCG      1065
His Thr Gly Val Val Arg Gly Pro Gly Leu Arg Trp Tyr Ala Leu Pro
    1755            1760            1765

GCC GTG TCC AAC ATG CTG CTG GAA ATC GGG GGT CTG GAG TTC TCC GCG      1113
Ala Val Ser Asn Met Leu Leu Glu Ile Gly Gly Leu Glu Phe Ser Ala
1770            1775            1780            1785

GCC CCC TTC AGC GGC TGG TAC ATG AGC ACG GAG ATT GGC ACG CGG AAC      1161
Ala Pro Phe Ser Gly Trp Tyr Met Ser Thr Glu Ile Gly Thr Arg Asn
                1790            1795            1800

CTG TGT GAC CCT CAC CGC TAC AAT ATC CTG GAG GAT GTG GCC GTC TGC      1209
Leu Cys Asp Pro His Arg Tyr Asn Ile Leu Glu Asp Val Ala Val Cys
            1805            1810            1815

ATG GAC CTC GAC ACG CGG ACC ACC TCG TCC CTG TGG AAG GAC AAG GCG      1257
Met Asp Leu Asp Thr Arg Thr Thr Ser Ser Leu Trp Lys Asp Lys Ala
        1820            1825            1830

GCC GTG GAG ATC AAC CTG GCT GTG CTG CAC AGC TTT CAG CTC GCC AAG      1305
Ala Val Glu Ile Asn Leu Ala Val Leu His Ser Phe Gln Leu Ala Lys
    1835            1840            1845

GTG ACC ATC GTG GAC CAC CAC GCC GCC ACG GTG TCC TTC ATG AAG CAC      1353
Val Thr Ile Val Asp His His Ala Ala Thr Val Ser Phe Met Lys His
1850            1855            1860            1865

CTG GAC AAC GAG CAG AAG GCC AGG GGG GGC TGC CCC GCC GAC TGG GCC      1401
Leu Asp Asn Glu Gln Lys Ala Arg Gly Gly Cys Pro Ala Asp Trp Ala
                1870            1875            1880

TGG ATC GTG CCC CCC ATC TAC GGC AGC CTA CCG CCC GTC TTC CAC CAG      1449
Trp Ile Val Pro Pro Ile Tyr Gly Ser Leu Pro Pro Val Phe His Gln
            1885            1890            1895
```

Fig. 3 continuation

```
GAG ATG GTC AAC TAC ATC CTG TCC CCT GCC TTC CGC TAC CAG CCA GAC        1497
Glu Met Val Asn Tyr Ile Leu Ser Pro Ala Phe Arg Tyr Gln Pro Asp
    1900            1905                1910

CCC TGG AAA GGG AGC GCG ACC AAG GGC GCC GGC ATC ACC AGG AAG AAG        1545
Pro Trp Lys Gly Ser Ala Thr Lys Gly Ala Gly Ile Thr Arg Lys Lys
    1915            1920                1925

ACC TTT AAG GAA GTG GCC AAC GCG GTG AAG ATC TCT GCC TCA CTC ATG        1593
Thr Phe Lys Glu Val Ala Asn Ala Val Lys Ile Ser Ala Ser Leu Met
1930            1935                1940                1945

GGC ACC CTG ATG GCC AAG CGA GTG AAA GCA ACC ATC CTG TAC GCC TCT        1641
Gly Thr Leu Met Ala Lys Arg Val Lys Ala Thr Ile Leu Tyr Ala Ser
                1950                1955                1960

GAG ACC GGC CGG GCC CAG AGC TAC GCT CAG CAG CTG GGG AGG CTC TTC        1689
Glu Thr Gly Arg Ala Gln Ser Tyr Ala Gln Gln Leu Gly Arg Leu Phe
                1965                1970                1975

CGG AAG GCC TTC GAT CCC CGG GTC CTG TGC ATG GAT GAG TAT GAC GTG        1737
Arg Lys Ala Phe Asp Pro Arg Val Leu Cys Met Asp Glu Tyr Asp Val
                1980                1985                1990

GTG TCC CTG GAG CAC GAG GCA CTG GTG CTG GTG GTG ACC AGC ACC TTT        1785
Val Ser Leu Glu His Glu Ala Leu Val Leu Val Val Thr Ser Thr Phe
            1995                2000                2005

GGG AAT GGC GAT CCC CCG GAG AAT GGA GAG AGT TTT GCA GCT GCC CTG        1833
Gly Asn Gly Asp Pro Pro Glu Asn Gly Glu Ser Phe Ala Ala Ala Leu
2010                2015                2020                2025

ATG GAG ATG TCG GGG CCC TAC AAC AGC TCC CCA CGG CCG GAA CAG CAC        1881
Met Glu Met Ser Gly Pro Tyr Asn Ser Ser Pro Arg Pro Glu Gln His
                2030                2035                2040

AAG AGT TAC AAG ATC CGC TTC AAC AGC GTC TCC TGC TCA GAC CCG CTG        1929
Lys Ser Tyr Lys Ile Arg Phe Asn Ser Val Ser Cys Ser Asp Pro Leu
                2045                2050                2055

GTG TCC TCC TGG CGG CGG AAG AGA AAG GAG TCC AGC AAC ACA GAC AGC        1977
Val Ser Ser Trp Arg Arg Lys Arg Lys Glu Ser Ser Asn Thr Asp Ser
            2060                2065                2070

GCG GGG GCC CTG GGG ACC CTC AGG TTC TGT GTG TTC GGA CTG GGC TCC        2025
Ala Gly Ala Leu Gly Thr Leu Arg Phe Cys Val Phe Gly Leu Gly Ser
    2075                2080                2085

CGG GCG TAC CCC CAC TTC TGC GCC TTC GCG CGA GCG GTG GAC ACC CGG        2073
Arg Ala Tyr Pro His Phe Cys Ala Phe Ala Arg Ala Val Asp Thr Arg
2090                2095                2100                2105

CTG GAA GAG CTT GGA GGG GAG CGG CTG CTG CAG CTG GGC CAG GGC GAT        2121
Leu Glu Glu Leu Gly Gly Glu Arg Leu Leu Gln Leu Gly Gln Gly Asp
                2110                2115                2120

GAG CTC TGC GGC CAG GAA GAG GCC TTC CGT GGT TGG GCA AAG GCG GCA        2169
Glu Leu Cys Gly Gln Glu Glu Ala Phe Arg Gly Trp Ala Lys Ala Ala
                2125                2130                2135
```

Fig. 3 continuation

```
TTC CAG GCC TCC TGC GAG ACG TTC TGC GTT GGG GAG GAG GCC AAG GCT      2217
Phe Gln Ala Ser Cys Glu Thr Phe Cys Val Gly Glu Glu Ala Lys Ala
        2140            2145                2150

GCT GCC CAG GAC ATC TTC AGC CCC AAA CGG AGC TGG AAA CGC CAG AGG      2265
Ala Ala Gln Asp Ile Phe Ser Pro Lys Arg Ser Trp Lys Arg Gln Arg
        2155            2160                2165

TAC CGG CTG AGC GCC CAG GCC GAG GGC CTC CAG CTG CTG CCA GGC CTG      2313
Tyr Arg Leu Ser Ala Gln Ala Glu Gly Leu Gln Leu Leu Pro Gly Leu
2170            2175                2180                2185

ATC CAC GTG CAC AGA CGG AAG ATG TTT CAG GCC ACA GTC CTC TCG GTG      2361
Ile His Val His Arg Arg Lys Met Phe Gln Ala Thr Val Leu Ser Val
                2190            2195                2200

GAA AAT CTG CAA AGC AGC AAG TCC ACC CGG GCC ACC ATC CTG GTG CGC      2409
Glu Asn Leu Gln Ser Ser Lys Ser Thr Arg Ala Thr Ile Leu Val Arg
                2205            2210                2215

CTG GAC ACT GCA GGC CAG GAG GGG CTG CAG TAC CAG CCG GGG GAC CAC      2457
Leu Asp Thr Ala Gly Gln Glu Gly Leu Gln Tyr Gln Pro Gly Asp His
        2220            2225                2230

ATA GGC ATC TCC GCG CCC AAC CGG CCG GGC CTG GTG GAG GCG CTG CTG      2505
Ile Gly Ile Ser Ala Pro Asn Arg Pro Gly Leu Val Glu Ala Leu Leu
        2235            2240                2245

AGC CGC GTG GAG GAC CCG CCA CCG CCC ACC GAG TCT GTG GCT GTG GAG      2553
Ser Arg Val Glu Asp Pro Pro Pro Pro Thr Glu Ser Val Ala Val Glu
2250            2255                2260                2265

CAG CTG GAG AAA GGC AGC CCA GGC GGC CCT CCT CCC AGC TGG GTG CGG      2601
Gln Leu Glu Lys Gly Ser Pro Gly Gly Pro Pro Pro Ser Trp Val Arg
                2270            2275                2280

GAC CCA CGG CTG CCC CCG TGC ACC GTG CGC CAG GCT CTC ACC TTC TTC      2649
Asp Pro Arg Leu Pro Pro Cys Thr Val Arg Gln Ala Leu Thr Phe Phe
                2285            2290                2295

CTG GAC ATC ACC TCC CCA CCC AGC CCC CGG CTT CTC CGA CTG CTC AGC      2697
Leu Asp Ile Thr Ser Pro Pro Ser Pro Arg Leu Leu Arg Leu Leu Ser
        2300            2305                2310

ACC CTG GCC GAA GAA CCC AGC GAG CAG CAG GAG CTT GAG ACC CTC AGT      2745
Thr Leu Ala Glu Glu Pro Ser Glu Gln Gln Glu Leu Glu Thr Leu Ser
        2315            2320                2325

CAG GAC CCC CGG CGC TAC GAG GAG TGG AAG TTG GTC CGC TGC CCC ACG      2793
Gln Asp Pro Arg Arg Tyr Glu Glu Trp Lys Leu Val Arg Cys Pro Thr
2330            2335                2340                2345

CTG CTG GAG GTG CTG GAG CAG TTC CCG TCC GTG GCG CTG CCC GCC CCG      2841
Leu Leu Glu Val Leu Glu Gln Phe Pro Ser Val Ala Leu Pro Ala Pro
                2350            2355                2360

CTG CTC CTC ACC CAG CTG CCC CTG CTG CAG CCC CGG TAC TAC TCT GTC      2889
Leu Leu Leu Thr Gln Leu Pro Leu Leu Gln Pro Arg Tyr Tyr Ser Val
                2365            2370                2375
```

Fig. 3 continuation

```
AGC TCG GCC CCC AAC GCC CAC CCC GGA GAG GTC CAC CTC ACA GTG GCC       2937
Ser Ser Ala Pro Asn Ala His Pro Gly Glu Val His Leu Thr Val Ala
        2380            2385                    2390

GTG CTG GCG TAC AGG ACC CAA GAT GGG CTG GGC CCC CTA CAC TAC GGG       2985
Val Leu Ala Tyr Arg Thr Gln Asp Gly Leu Gly Pro Leu His Tyr Gly
    2395                2400                    2405

GTC TGC TCC ACA TGG CTG AGC CAG CTC AAG ACT GGA GAC CCC GTG CCC       3033
Val Cys Ser Thr Trp Leu Ser Gln Leu Lys Thr Gly Asp Pro Val Pro
2410                2415                2420                2425

TGC TTC ATC AGG GGG GCT CCC TCC TTC CGG CTG CCG CCT GAC CCC TAC       3081
Cys Phe Ile Arg Gly Ala Pro Ser Phe Arg Leu Pro Pro Asp Pro Tyr
                2430                2435                2440

GTG CCC TGC ATC CTC GTG GGC CCT GGC ACT GGC ATC GCC CCC TTC CGG       3129
Val Pro Cys Ile Leu Val Gly Pro Gly Thr Gly Ile Ala Pro Phe Arg
            2445                2450                2455

GGA TTT TGG CAG GAG AGG CTG CAT GAC ATT GAG AGC AAA GGG CTG CAG       3177
Gly Phe Trp Gln Glu Arg Leu His Asp Ile Glu Ser Lys Gly Leu Gln
        2460                2465                2470

CCG CAC CCC ATG ACC CTG GTG TTC GGC TGC CGC TGC TCC CAA CTC GAC       3225
Pro His Pro Met Thr Leu Val Phe Gly Cys Arg Cys Ser Gln Leu Asp
    2475                2480                2485

CAT CTC TAC CGC GAC GAG GTG CAG GAC GCC CAG GAG CGC GGG GTG TTT       3273
His Leu Tyr Arg Asp Glu Val Gln Asp Ala Gln Glu Arg Gly Val Phe
2490                2495                2500                2505

GGC CGC GTC CTC ACC GCC TTC TCC CGG GAA CCT GAC AGC CCC AAG ACC       3321
Gly Arg Val Leu Thr Ala Phe Ser Arg Glu Pro Asp Ser Pro Lys Thr
                2510                2515                2520

TAC GTA CAG GAC ATC CTG AGA ACC GAG CTG GCT GCC GAG GTG CAC CGC       3369
Tyr Val Gln Asp Ile Leu Arg Thr Glu Leu Ala Ala Glu Val His Arg
            2525                2530                2535

GTG CTG TGC CTC GAG CGG GGC CAC ATG TTT GTC TGC GGC GAT GTC ACT       3417
Val Leu Cys Leu Glu Arg Gly His Met Phe Val Cys Gly Asp Val Thr
        2540                2545                2550

ATG GCA ACC AGC GTC CTG CAG ACG GTG CAG CGC ATC TTG GCG ACA GAG       3465
Met Ala Thr Ser Val Leu Gln Thr Val Gln Arg Ile Leu Ala Thr Glu
    2555                2560                2565

GGC GAC ATG GAG CTG GAC GAG GCG GGC GAC GTC ATC GGC GTG CTG CGG       3513
Gly Asp Met Glu Leu Asp Glu Ala Gly Asp Val Ile Gly Val Leu Arg
2570                2575                2580                2585

GAT CAG CAA CGC TAT CAC GAG GAC ATT TTC GGC CTC ACG CTG CGC ACC       3561
Asp Gln Gln Arg Tyr His Glu Asp Ile Phe Gly Leu Thr Leu Arg Thr
                2590                2595                2600

CAG GAG GTG ACA AGC CGT ATA CGT ACC CAG AGC TTT TCC CTG CAG GAG       3609
Gln Glu Val Thr Ser Arg Ile Arg Thr Gln Ser Phe Ser Leu Gln Glu
            2605                2610                2615
```

Fig. 3 continuation

```
CGG CAT CTG CGG GGC GCG GTG CCC TGG GCC TTC GAC CCG CCC GGC CCA              3657
Arg His Leu Arg Gly Ala Val Pro Trp Ala Phe Asp Pro Pro Gly Pro
        2620                2625                    2630

GAC ACC CCC GGC CCC TGAGACCCCT CTTGCTTCCC ACTGCAGTTC CCGGAGAGAG              3712
Asp Thr Pro Gly Pro
        2635

GGGCTGTCAT TCCACTATGG CTCTACCGCT GTCCTGTTGG CCTTTACCGG GACCGGCCAC            3772

CTCTCCCTCC CCTCCCAAGG TGACTTCCCA GAGACTGTTG GATTCCCTGT ACTATCTCAT            3832

CCTCTCATCT CTAGGTCTGT TTCCCCACCC TAAGTCCATC TGGAAGACCC CTCCCAGCAG            3892

CGGTATTCCA GAGCCTACAG TCAGCCCTTT GGTGTTTAGG TGAATTTTAG ATTCCCCTCG            3952

CCTCTCTCCC GGGAAGTATC TTATCTTGAA ACCTGATCTC TAAATCATTC AAATATTTAT            4012

TATTGAAGAT TTACCATAAG AGACTGGACC AGAAGTTAGG AGACCTACTA AGATGCCTAA            4072

GCCAAGGTCC TCCGGGGCCG AATTC                                                  4097
``` pSP65h-CMV1 (2166 bps)

PSCT GALX-556         (2802 bps)

iNOS         (3970 bps)

DNA EXPRESSION VECTORS FOR THE USE IN THE GENE THERAPEUTIC TREATMENT OF VASCULAR DISORDERS

This is a continuation application of Ser. No. 08/553,503 filed Mar. 1, 1996, abandoned, which is the national phase application of PCT/EP95/01202 filed Mar. 31, 1995 claiming priority of German Application P4411402.8 filed Mar. 31, 1994. The subject matter of each of these applications is hereby incorporated by reference.

The invention relates to the use of DNA expression vectors for gene therapeutic treatment of vascular disorders such as high blood pressure, arteriosclerosis, stenosis or restenosis.

BACKGROUND OF THE INVENTION

As percutaneous, transluminal coronary angioplasty (PTCA), one understands a method which is widely employed in the clinic in which the critical constriction of a coronary vessel (coronary stenosis) is mechanically dilated by a catheter and therewith made free again. To this day, the Achilles heal of PTCA is restenosis. This appears after weeks or months after successful PTCA in 12–43% of all treated patients (Lange, R. A. et al., Southwestern Internal Medicine Conference: Restenosis: The Achilles heal of coronary angioplasty, Am. J. Med. Sci., 265–274, 1993). A renewed PTCA or a bypass operation is the necessary consequence.

In the final analysis, the exact mechanism of restenosis is unexplained. However, of importance is the initial mechanical stretching stimulus in which, aside from destruction of the endothelial cells, tearing occurs in the arteriosclerotic wall region with simultaneous deposition of fibrin and blood platelets. The blood platelets on their part release vessel constricting and proliferation increasing metabolic products which veil the growth inhibiting factors of the smooth vessel musculature. A hyperplasty of the muscle media, i.e. restenosis, is the result.

Various strategies for the treatment of restenosis were examined in clinical studies in the past. Concerning pharmacological therapy, neither the use of anti-thrombotic agents (aspirin, heparin), antispastic agents (nifedipin, diltazem) or antiproliferative agents (colchicine) nor a lipid level sinking therapy had a favorable influence on the development of the restenosis. The development of new catheters for the minimalisation of tissue trauma (laser angioplasty, atherectomy catheter) has also brought no success in the prevention of restenosis.

There is no therapy for restenosis at the present. The reason is probably because the effective levels in blood after systemic application of a drug are too low to be able to be locally therapeutically effective.

Nitrogen monoxide (NO) is formed in mammalian cells from the amino acid L-arginine through the mediation of the enzyme NO synthase (NOS). NO is an important messenger substance and/or signal molecule in the human body which mediates a multitude of physiological and pathophysiological effects. In the central nervous system, NO is probably involved in the regulation of integrative performance, i.e. memory functions. In the gastrointestinal tract, an involvement in peristalsis is suspected. The NO formed by macrophages is capable of killing bacteria and parasites. Within the heart-circulatory system, NO is formed from the endothelial cells where it carries out two important functions. In the direction of the luminal side of the vessel it inhibits platelet aggregation and is therewith jointly responsible for the antithrombogenic properties of the vessel inner wall. On the side away from the lumen NO relaxes the smooth musculature and carries out a long-term proliferation inhibiting effect. An abolition of the endothelial NO, for example by injury of the blood vessel endothelium, leads to high blood pressure in the entire organism and is probably involved in the development of arteriosclerosis. In addition, it is important for the function of NO that its biological half-life is shorter than one second. Therewith, NO can only reach the cells in the immediate neighborhood of the location of formation, i.e. the effect of NO is locally limited.

At least three different NOS isozymes belong to the family of NOS: the endothelial enzyme (eNOS), the brain enzyme (bNOS) and the inducible NOS (iNOS). All three isozymes are isolated by now, their primary structure, i.e. amino acid sequence, solved and the coding gene segments characterized. The essential difference between these NOS lies in their molecular weight and above all in the regulation of the expression and the enzymatic activity. Thus, eNOS and bNOS are regulated through their activity and iNOS chiefly through expression.

For the characterization of the NOS enzymes the following is illustrated:

eNOS: this enzyme has a molecular weight of 133 kDa, has a binding site for calmodulin which is dependent on free $Ca^{++}$ concentration and is present to more than 90% as membrane bound.

bNOS: the brain enzyme is a homodimer with a molecular weight of 160 kDa per subunit which is present at less than 10% as membrane bound. As with the eNOS, the calmodulin binding is dependent on free $Ca^{++}$, i.e. both enzymes are only active when the intracellular $Ca^{++}$ concentration is increased, for example as a result of a receptor mediated $Ca^{++}$ influx.

iNOS: the inducible NOS is also a homodimer with a molecular weight of 130 kDa per subunit. The essential difference to the other isozymes is that the activity of iNOS is independent from calmodulin and therewith independent from cellular calcium. Because the turnover rate for L-arginine for iNOS is approximately 10–100 times higher than by eNOS and bNOS, iNOS is also referred to as "high output" NOS. Under basal conditions, iNOS can not normally be detected; it is however strongly expressed after immunological activation through inflammation mediators and endotoxins.

OBJECTS OF THE INVENTION

Object of the present invention is to make an expression vector available which is suitable for gene therapeutic treatment of vascular disorders, especially high blood pressure or arteriosclerosis, stenosis or restenosis.

SUMMARY OF THE INVENTION

The above object is solved by a DNA expression vector that comprises a DNA sequence which codes for a protein which expresses the biological activity of nitrogen monoxide synthase and comprises eukaryotic regulation elements, wherein the blood vessels transformed or infected with this DNA expression vector express recombinant nitrogen monoxide synthase in a therapeutically acceptable amount for the inhibition of stenosis or restenosis of said blood vessels and/or for the inhibition of the proliferation of the smooth vessel musculature.

The above expression vector finds use according to the invention in a method for the treatment of vascular disorders, particularly high blood pressure, arteriosclerosis or stenosis, and especially for restenosis of the coronary vessels after percutaneous, transluminal coronary angioplasty.

Furthermore, a pharmaceutical composition is made available.

The inventors have surprisingly found that the expression of recombinant nitrogen monoxide synthase in blood vessels which were transfected with a DNA expression vector described here leads to a therapeutically relevant inhibition of vessel stenosis and restenosis after percutaneous, transluminal coronary angioplasty.

The invention relates to a DNA sequence, preferably a cDNA sequence, which is obtained from mammals, preferably mice or humans, which codes for iNOS, bNOS or eNOS, preferably iNOS, activity. The iNOS cDNA is preferably employed because it has a higher specific activity which is furthermore Ca independent. The enzyme activity is therefore independent from regulatory influences.

The DNA expression vector can comprise a sequence element which allows replication in bacteria, a sequence element which allows the replication of said vector in eukaryotic cells, preferably the SV40 replication sequence element, a polyadeylation signal and one or more introns.

The regulation element can comprise the promoter and/or the enhancer region from eukaryotic viruses, preferably from Cytomegalovirus or Adenovirus, and more preferably the promoter-enhancer of the Cytomegalovirus immediate early polypeptide gene.

Additionally, the present invention relates to the treatment and prevention of vascular disorders in humans such as high blood pressure and arteriosclerosis as well as stenosis or restenosis of the blood vessels. The invention particularly relates to a method for the treatment and prevention of restenosis of the coronary vessels after percutaneous, transluminal coronary angioplasty (PTCA), whereby the blood vessels are brought into contact, transfected, or infected with the DNA expression vector described above.

The transfection or infection of the blood vessels with a DNA expression vector can occur by every standard method known in the art and is not limited to the transfection techniques described here.

Furthermore, the invention relates to a pharmaceutical composition which comprise this DNA expression vector for the treatment or prevention of the above mentioned vascular disorders. The pharmaceutical composition can comprise a pharmaceutically acceptable carrier, a stabilizing agent or buffer in addition to the DNA expression vector. The following Figures serve to illustrate the invention.

BRIEF DESCRIPTION OF THE FIGURES

FIG. 1 Nucleotide (SEQ. ID NO: 1) and amino acid (SEQ. ID NO: 2) sequence of the inducible NO synthase of mouse (Mus musculus/mammalia deduced from the cloned cDNA, Genbank Accession No.: M92649);

DETAILED DESCRIPTION OF THE INVENTION

Figure 4A:
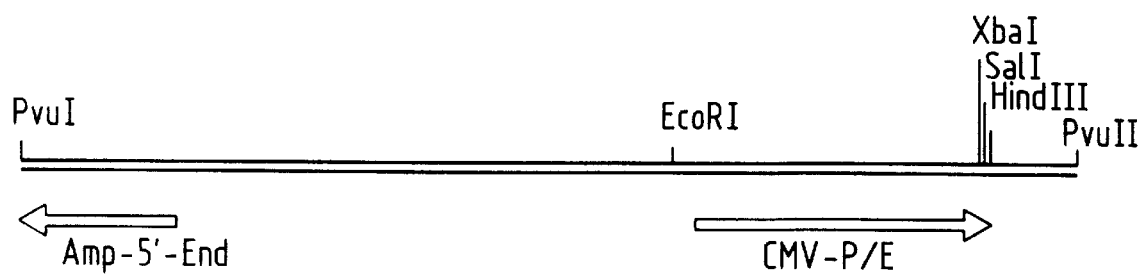
Figure 4B:
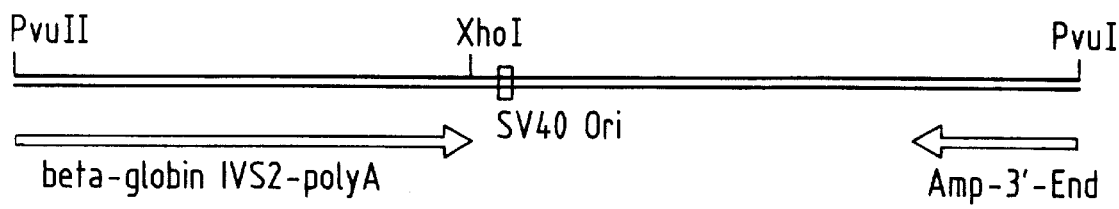
Figure 4C:
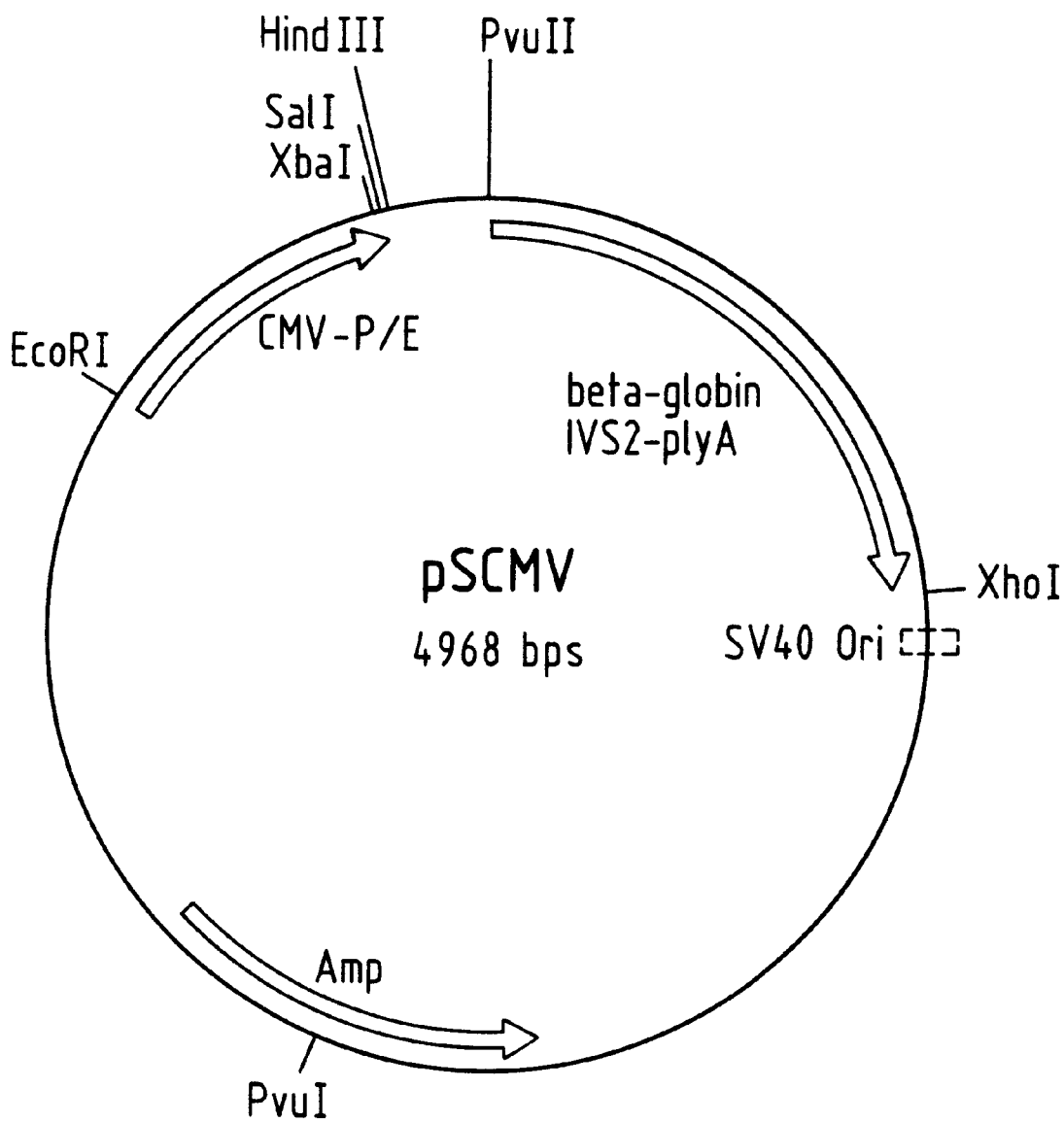
Figure 4D:
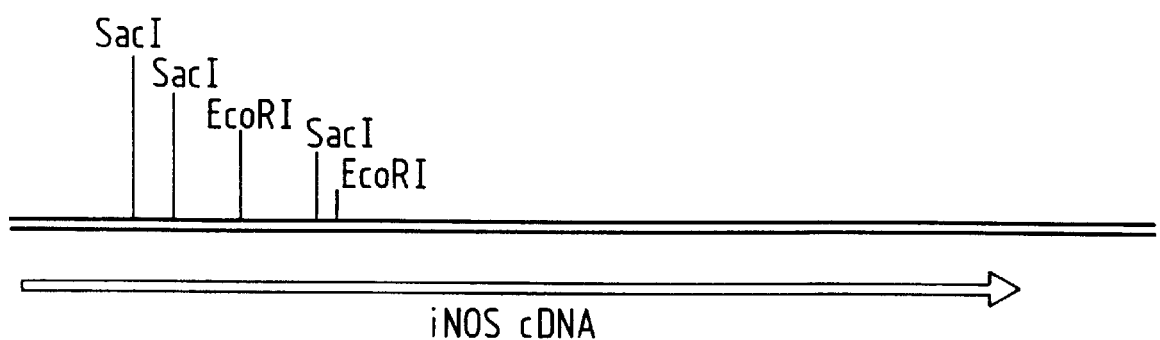
Figure 4E:
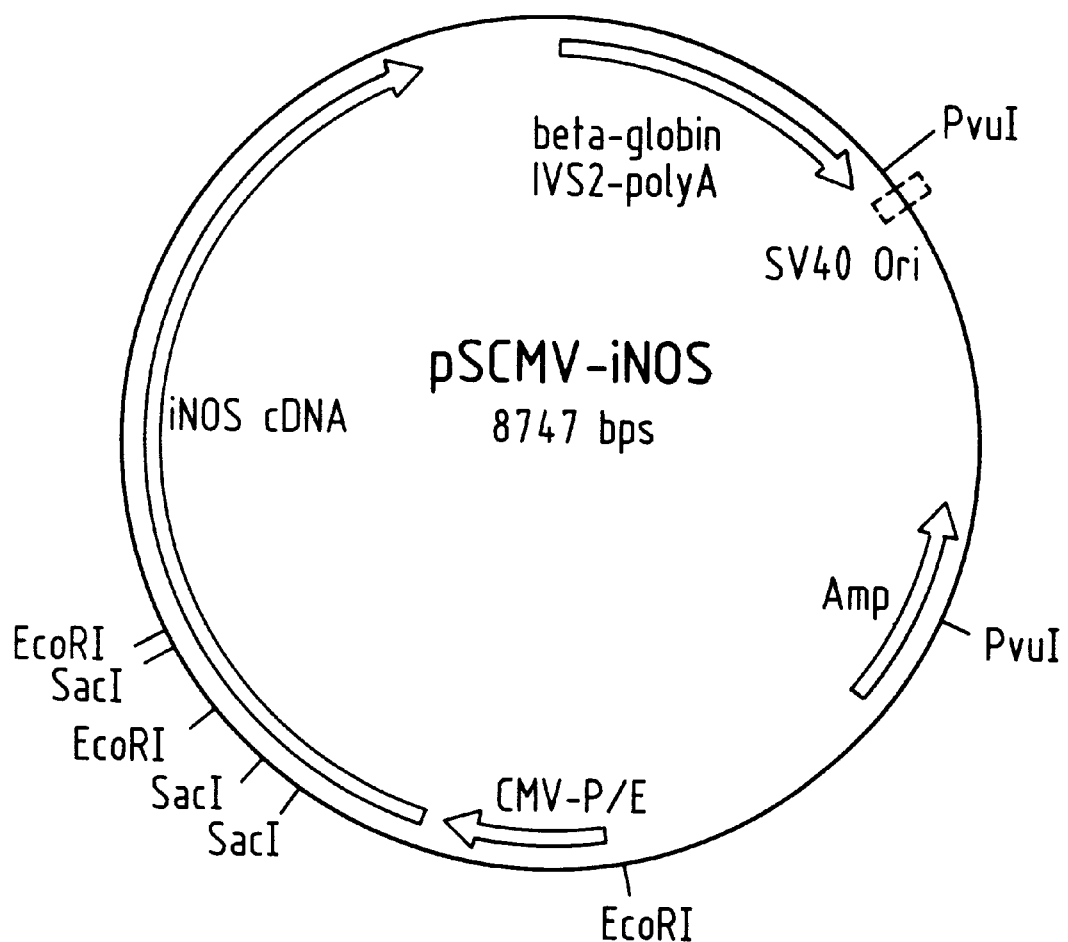

FIG. 2 Nucleotide (SEQ. ID NO: 3) and amino acid (SEQ. ID NO: 4) sequence of the neuronal NO synthase of human (Homo sapiens/mammalia deduced from the cloned cDNA, Genbank Accession No.: L02881);

FIG. 3 Nucleotide (SEQ. ID NO: 5) and amino acid (SEQ. ID NO: 6) sequence of the endothelial NO synthase of bovine (Bos taurus/mammalia deduced from the cloned cDNA, Genbank Accession No.: M95674);

FIG. 4a the 2.17 Kb CMV promoter containing PvuI-PvuII fragment which was isolated from the plasmid pSP65h-CMV for the further construction of the plasmid pSCMV;

FIG. 4b the PvuI-PvuII fragment containing the 2.80 Kb 3' region of the β-globin gene and the SV40 origin of replication which was isolated from the plasmid pSCT GAL X-556 for the further construction of the plasmid pCMV;

FIG. 4c the plasmid pSCMV;

FIG. 4d the 3.97 Kb iNOS containing HindIII-XhoI fragment according to FIG. 1;

FIG. 4e the plasmid pSCMV-iNOS.

The following Examples should more closely illustrate the invention without limiting it to them.

EXAMPLE 1

I. Elements of an Expression Vector

The expression plasmid pSCMV-iNOS was cloned based on the plasmid pSO65 (Promega Biotech). It contains the following functional elements:

promoter/enhancer of the human Cytomegalovirus immediate early polypeptide (Pos. 216-809/Genbank Accession No.: K03104)

cDNA of the inducible NO synthase of the mouse (Pos. 127-4110/Genbank Accession No.: M92649)

genomic sequences of β-globin gene of rabbit (Pos. 905-2080) which contains intron 2, exon 3 and the polyadenylation signal (Pos. 905-1827 are stored under Genbank Accession No.: J00659)

the origin of replication of SV40 virus (Pos. 130 [SV40 early map] or Pos. 5176-130 of the circular SV40 map/Genbank Accession No.: V01380).

II. Production of an Expression Vector:

The CMV promoter/enhancer was present as a DNA fragment inserted in the SmaI site of the plasmids pSP65 with blunt ends (pSP65h-CMV1). The PvuI-PvuII fragment was isolated from this plasmid which carries the CMV promoter (FIG. 4a).

A PvuI-PvuII fragment which carries the 3' region of the β-globin gene and the SV40 origin of replication (FIG. 4b) was isolated from the plasmid PSCT GAL.X-556 (see FIG. 4b). This fragment was ligated with the PvuI-PvuII fragment from pSP65h-CMV1. From the resulting plasmid (pSCMV, FIG. 4c), the following alterations were performed:

deletion of the vector sequences between HindIII and PvuII with simultaneous insertion of a ClaI linker. Thereby, the starting cleavage sites PvuII and HindIII were lost.

conversion of the XhoI cleavage site into a PvuI cleavage site.

The vector obtained is designated as pSCMV2.

The iNOS cDNA was cloned as a HindIII-XhoI fragment in the XbaI-SalI digested vector pSCMV2 (FIG. 4d). Additionally, the 5' overhanging ends were converted to blunt ends by filling in after the XbaI digestion. At the 3' end, the cDNA was fused with the intron and the polyadenylation signal of the β-globin gene from chicken. The functionality of the construct was verified by transfection of COS cells and subsequently by detection of the enzyme activity. The resulting plasmid pSCMV-iNOS (FIG. 4e) was employed for the transfection experiments. The CMV promoter imparts a constitutive expression of the iNOS gene. The activity of the enzyme made is Ca independent.

III. Production of DNA Liposome Complexes

The cultivation of Sendi virus occurred in the chorionallantis fluid of fertilized chicken eggs (d10–d12 of the embryonic development) according to standard methods (Nakanishi M., Uchida T., Sugawa H., Ishiura M., Okada Y., Exp. Cell Res. 159, 399–409).

Phosphatidylcholine, phosphatidylserine and cholesterol were dissolved in tetrahydrofuran, mixed in a molar ratio of 4.8:1:2 and evaporated under nitrogen. 10 mg of the dried lipids were suspended by vortexing in 200 μl pSCMV-iNOS [dissolved in BSS (140 mM NaCl, 5.4 mM KCl and 10 mM Tris-HCl, pH 7.69)] (conc. 1 μg/ul). The liposomes obtained were incubated with 4 ml Sendi virus (Z strain) (16000 hemagglutination units (HAU)/ml) for 3 h at 37° C. under light shaking and subsequently sonicated for 20" in the ultrasonic bath. The viruses were inactivated before use with UV light (11 $J/m^2 \times s$). The suspension obtained was loaded on two saccharose gradients (1 ml 60%, 1 ml 40%, 8 ml 30% saccharose in BSS) and centrifuged for 3 h at 30,000 rpm in the SW40 rotor (Beckman Instruments) at 4° C. The top 2 ml were collected and employed for the transfection experiments.

IV. Transfection Protocol

To investigate the effects of a local over-expression of iNOS on the proliferation of the smooth vessel musculature after endothelial injury in vivo, the established restenosis rat model of Clowes AW, Reidy MA and Clowes MM (Lab. Invest. 49, 327–333, 1983) was used. In the neck region, the common carotid artery was prepared as well as the rostral lying bifurcation at which the common carotid artery branches into the external carotid artery and internal carotid artery. The external carotid artery was permanently ligated approximately 1 cm rostral from the bifurcation; the internal carotid artery was temporarily ligated by a vessel clamp. The external carotid artery was opened by a cut approximately 0.5 cm rostral from the bifurcation. A Fogarty 2F embolectomy catheter was lead into the common carotid artery through this opening and the endothelium of the common carotid artery was removed by three passages of the dilated catheter.

For the "therapy group", the following method was used. The denuded vessel was closed with a vessel clamp 1.5 to 2 cm caudal from the bifurcation after the removal of the catheter. A polyethylene catheter was integrated in the vessel from the opening in the external carotid artery. Through this catheter 50–100 μl of a solution with DNA liposome complexes were injected within 15–20 min. into the isolated section of the common carotid artery. Care was taken that the vessel section stood under pressure from the liposome solution during the transfection. After removal of the transfection catheter, the external carotid artery was permanently ligated caudal to the vessel incision, and subsequently, the blood flow over the common carotid artery and internal carotid artery was re-established by removal of the vessel clamps.

V. Morphological Analysis of the Vessels

At various time points after the transfection of the common carotid artery (to 21 d), rats were examined with respect to the morphological changes in the vessels. The vessels were fixed by perfusion with 3% paraformaldehyde in PBS (140 mM NaCl, 10 mM Na phosphate, pH 7.5) and sectioned. The degree of the proliferation was compared with control treated vessels. A reduction of the stenosis formation by up to 60% in the treated animals was demonstrated. This study shows for the first time that in this animal model the local over-expression of a gene results in a therapeutically relevant inhibition of vessel stenosis and demonstrates the special roll of NO for the inhibition of the proliferation of smooth vessel musculature.

What is claimed is:

1. A pharmaceutical composition for the treatment and prevention of vascular disorders which comprises a pharmaceutically acceptable carrier and, as an active ingredient, a pharmaceutical agent comprising a DNA sequence encoding inducible nitrogen monoxide synthase (iNOS) and eukaryotic regulation elements which result in the expression of said DNA sequence in eukaryotic cells, wherein the pharmaceutical agent is complexed to liposomes.

2. The pharmaceutical composition as claimed in claim 1, wherein the DNA sequence encoding inducible nitrogen monoxide synthase (iNOS) is a cDNA sequence.

3. The pharmaceutical composition as claimed in claim 1, wherein the eukaryotic regulation elements are derived from a eukaryotic virus.

4. The pharmaceutical composition according to claim 1, wherein the eukaryotic regulation elements are derived from an Adenovirus promoter and/or enhancer element.

5. The pharmaceutical composition as claimed in claim 1, wherein the eukaryotic regulation elements are derived from a Cytomegalovirus (CMV) promoter and/or enhancer of the immediate early gene.

6. The pharmaceutical composition as claimed in claim 1 or 2, wherein the DNA or cDNA sequence is a mammalian sequence.

7. The pharmaceutical composition as claimed in claim 3, wherein the eukaryotic virus is Cytomegalovirus or Adenovirus.

8. The pharmaceutical composition as claimed in claim 6, wherein the DNA or cDNA sequence constitutes a human DNA or cDNA sequence.

9. The pharmaceutical composition as claimed in claim 6, wherein the DNA or cDNA sequence constitutes a mouse DNA or cDNA sequence.

10. A pharmaceutical composition for the treatment and prevention of high blood pressure, arteriosclerosis, stenosis and restenosis comprising as an active ingredient a DNA expression vector which comprises a DNA sequence encoding inducible nitrogen monoxide synthase (iNOS) and eukaryotic regulation elements, wherein the expression vector is complexed to liposomes.

11. The pharmaceutical composition as claimed in claim 10, wherein the DNA sequence encoding inducible nitrogen monoxide synthase (iNOS) is a cDNA sequence.

12. The pharmaceutical composition as claimed in claim 10, wherein the expression vector further comprises a DNA sequence that allows replication in bacteria, a DNA sequence encoding the SV40 replication sequence element and a polyadenylation signal.

13. The pharmaceutical composition as claimed in claim 10, wherein the eukaryotic regulation elements are derived from a eukaryotic virus.

14. The pharmaceutical composition as claimed in claim 10, wherein the DNA expression vector is pSCMV-iNOS according to FIG. 4e.

15. The pharmaceuticals composition as claimed in claims 10 or 11, wherein the DNA or cDNA sequence is a mammalian sequence.

16. The pharmaceutical composition as claimed in claim 13, wherein the eukaryotic virus is Cytomegalovirus or Adenovirus.

17. The pharmaceutical composition as claimed in claim 15, wherein the DNA or cDNA sequence constitutes a human DNA or cDNA sequence.

18. The pharmaceutical composition as claimed in claim 15, wherein the DNA or cDNA sequence constitutes a mouse DNA or cDNA sequence.

* * * * *

SEQUENCE LISTING

<160> NUMBER OF SEQ ID NOS: 6

<210> SEQ ID NO 1
<211> LENGTH: 4110
<212> TYPE: DNA
<213> ORGANISM: Mus musculus

<400> SEQUENCE: 1

```
gagactctgg ccccacggga cacagtgtca ctggtttgaa acttctcagc caccttggtg      60
aagggactga gctgttagag acacttctga ggctcctcac gcttgggtct tgttcactcc     120
acggagtagc ctagtcaact gcaagagaac ggagaacgtt ggatttggag cagaagtgca     180
aagtctcaga catggcttgc ccctggaagt ttctcttcaa agtcaaatcc taccaaagtg     240
acctgaaaga ggaaaaggac attaacaaca acgtgaagaa aaccccttgt gctgttctca     300
gcccaacaat acaagatgac cctaagagtc accaaaatgg ctccccgcag ctcctcactg     360
ggacagcaca gaatgttcca gaatccctgg acaagctgca tgtgacatcg acccgtccac     420
agtatgtgag gatcaaaaac tggggcagtg gagagatttt gcatgacact cttcaccaca     480
aggccacatc ggatttcact tgcaagtcca agtcttgctt ggggtccatc atgaacccca     540
agagtttgac cagaggaccc agagacaagc ctaccctct ggaggagctc ctgcctcatg     600
ccattgagtt catcaaccag tattatgcgct cctttaaaga ggcaaaaata gaggaacatc     660
tggccaggct ggaagctgta acaaaggaaa tagaaacaac aggaaccttac cagctcactc     720 tggatgagct catctttgcc accaagatgg cctggaggaa tgccctcgc tgcatcggca     780
```

```
ggatccagtg gtccaacctg caggtctttg acgctcggaa ctgtagcaca gcacaggaaa      840
tgtttcagca catctgcaga cacatacttt atgccaccaa caatggcaac atcaggtcgg      900
ccatcactgt gttcccccag cggagtgacg gcaaacatga cttcaggctc tggaattcac      960
agctcatccg gtacgctggc taccagatgc ccgatggcac catcagaggg gatgctgcca     1020
ccttggagtt cacccagttg tgcatcgacc taggctggaa gccccgctat ggccgctttg     1080
atgtgctgcc tctggtcttg caagctgatg gtcaagatcc agaggtcttt gaaatccctc     1140
ctgatcttgt gttggaggtg accatggagc atcccaagta cgagtggttc caggagctcg     1200
ggttgaagtg gtatgcactg cctgccgtgg ccaacatgct actggaggtg ggtggcctcg     1260
aattcccagc ctgcccttc aatggttggt acatgggcac cgagattgga gttcgagact      1320
tctgtgacac acagcgctac aacatcctgg aggaagtggg ccgaaggatg ggcctggaga     1380
cccacacact ggcctccctc tggaaagacc gggctgtcac ggagatcaat gtggctgtgc     1440
tccatagttt ccagaagcag aatgtgacca tcatggacca ccacacagcc tcagagtcct     1500
tcatgaagca catgcagaat gagtaccggg cccgtggagg ctgcccggca gactggattt     1560
ggctggtccc tccagtgtct gggagcatca cccctgtgtt ccaccaggag atgttgaact     1620
atgtcctatc tccattctac tactaccaga tcgagccctg gaagacccac atctggcaga     1680
atgagaagct gaggcccagg aggagagaga tccgatttag agtcttggtg aaagtggtgt     1740
tctttgcttc catgctaatg cgaaaggtca tggcttcacg ggtcagagcc acagtcctct     1800
ttgctactga gacagggaag tctgaagcac tagccaggga cctggccacc ttgttcagct     1860
acgccttcaa caccaaggtt gtctgcatgg accagtataa ggcaagcacc ttggaagagg     1920
agcaactact gctggtggtg acaagcacat ttgggaatgg agactgtccc agcaatgggc     1980
agactctgaa gaaatctctg ttcatgctta gagaactcaa ccacaccttc aggtatgctg     2040
tgtttggcct tggctccagc atgtaccctc agttctgcgc ctttgctcat gacatcgacc     2100
agaagctgtc ccacctggga gcctctcagc ttgccccaac aggagaaggg gacgaactca     2160
gtgggcagga ggatgccttc cgcagctggg ctgtacaaac cttccgggca gcctgtgaga     2220
cctttgatgt ccgaagcaaa catcacattc agatcccgaa acgcttcact tccaatgcaa     2280
catgggagcc acagcaatat aggctcatcc agagcccgga gcctttagac ctcaacagag     2340
ccctcagcag catccatgca aagaacgtgt ttaccatgag gctgaaatcc agcagaatc      2400 tgcagagtga aaagtccagc cgcaccaccc tcctcgttca gctcaccttc gagggcagcc     2460
gagggcccag ctacctgcct ggggaacacc tggggatctt cccaggcaac cagaccgccc     2520
tggtgcaggg aatcttggag cgagttgtgg attgtcctac accacaccaa actgtgtgcc     2580
tggaggttct ggatgagagc ggcagctact gggtcaaaga caagaggctg ccccctgct      2640 cactcagcca agccctcacc tacttcctgg acattacgac ccctcccacc cagctgcagc     2700
tccacaagct ggctcgcttt gccacggacg agacggatag gcagagattg gaggccttgt     2760
gtcagccctc agagtacaat gactggaagt tcagcaacaa ccccacgttc tggaggtgc      2820 ttgaagagtt cccttccttg catgtgcccg ctgccttcct gctgtcgcag ctccctatct     2880
tgaagccccg ctactactcc atcagctcct cccaggacca caccccctcg gaggttcacc     2940
tcactgtggc cgtggtcacc taccgcaccc gagatggtca gggtcccctg caccatggtg     3000
tctgcagcac ttggatcagg aacctgaagc cccaggaccc agtgccctgc tttgtgcgaa     3060
gtgtcagtgg cttccagctc cctgaggacc cctcccagcc ttgcatcctc attgggcctg     3120
```

-continued

```
gtacgggcat tgctcccttc cgaagtttct ggcagcagcg gctccatgac tcccagcaca    3180
aagggctcaa aggaggccgc atgagcttgg tgtttgggtg ccggcacccg gaggaggacc    3240
acctctatca ggaagaaatg caggagatgg tccgcaagag agtgctgttc caggtgcaca    3300
caggctactc ccggctgccc ggcaaaccca aggtctacgt tcaggacatc gtgcaaaagc    3360
agctggccaa tgaggtactc agcgtgctcc acggggagca gggccacctc tacatttgcg    3420
gagatgtgcg catggctcgg gatgtggcta ccacattgaa gaagctggtg gccaccaagc    3480
tgaacttgag cgaggagcag gtggaagact atttcttcca gctcaagagc cagaaacgtt    3540
atcatgaaga tatcttcggt gcagtctttt cctatggggc aaaaaagggc agcgccttgg    3600
aggagcccaa agccacgagg ctctgacagc ccagagttcc agcttctggc actgagtaaa    3660
gataatggtg aggggcttgg ggagacagcg aaatgcaatc ccccccaagc ccctcatgtc    3720 attccccccct cctccaccct accaagtagt attgtattat tgtggactac taaatctctc    3780
tcctctcctc cctcccctct ctcccttttcc tcccttcttc tccactcccc agctccctcc    3840
ttctccttct cctcctttgc ctctcactct tccttggagc tgagagcaga gaaaaactca    3900
acctcctgac tgaagcactt tgggtcacca ccaggaggca ccatgccgcc gctctaatac    3960
ttagctgcac tatgtacaga tatttatact tcatatttaa gaaaacagat acttttgtct    4020
actcccaatg atggcttggg cctttcctgt ataattcctt gatgaaaaat atttatataa    4080
aatacatttt attttaatca aaaaaaaaa                                     4110
```

<210> SEQ ID NO 2
<211> LENGTH: 1144
<212> TYPE: PRT
<213> ORGANISM: Mus musculus

<400> SEQUENCE: 2

```
Met Ala Cys Pro Trp Lys Phe Leu Phe Lys Val Lys Ser Tyr Gln Ser
 1               5                  10                  15

Asp Leu Lys Glu Glu Lys Asp Ile Asn Asn Asn Val Lys Lys Thr Pro
            20                  25                  30

Cys Ala Val Leu Ser Pro Thr Ile Gln Asp Asp Pro Lys Ser His Gln
        35                  40                  45

Asn Gly Ser Pro Gln Leu Leu Thr Gly Thr Ala Gln Asn Val Pro Glu
    50                  55                  60

Ser Leu Asp Lys Leu His Val Thr Ser Thr Arg Pro Gln Tyr Val Arg
65                  70                  75                  80

Ile Lys Asn Trp Gly Ser Gly Glu Ile Leu His Asp Thr Leu His His
                85                  90                  95

Lys Ala Thr Ser Asp Phe Thr Cys Lys Ser Lys Ser Cys Leu Gly Ser
            100                 105                 110

Ile Met Asn Pro Lys Ser Leu Thr Arg Gly Pro Arg Asp Lys Pro Thr
        115                 120                 125

Pro Leu Glu Glu Leu Leu Pro His Ala Ile Glu Phe Ile Asn Gln Tyr
    130                 135                 140

Tyr Gly Ser Phe Lys Glu Ala Lys Ile Glu Glu His Leu Ala Arg Leu
145                 150                 155                 160

Glu Ala Val Thr Lys Glu Ile Glu Thr Thr Gly Thr Tyr Gln Leu Thr
                165                 170                 175

Leu Asp Glu Leu Ile Phe Ala Thr Lys Met Ala Trp Arg Asn Ala Pro
            180                 185                 190

Arg Cys Ile Gly Arg Ile Gln Trp Ser Asn Leu Gln Val Phe Asp Ala
```

-continued

```
            195                 200                 205
Arg Asn Cys Ser Thr Ala Gln Glu Met Phe Gln His Ile Cys Arg His
    210                 215                 220

Ile Leu Tyr Ala Thr Asn Asn Gly Asn Ile Arg Ser Ala Ile Thr Val
225                 230                 235                 240

Phe Pro Gln Arg Ser Asp Gly Lys His Asp Phe Arg Leu Trp Asn Ser
                245                 250                 255

Gln Leu Ile Arg Tyr Ala Gly Tyr Gln Met Pro Asp Gly Thr Ile Arg
                260                 265                 270

Gly Asp Ala Ala Thr Leu Glu Phe Thr Gln Leu Cys Ile Asp Leu Gly
            275                 280                 285

Trp Lys Pro Arg Tyr Gly Arg Phe Asp Val Leu Pro Leu Val Leu Gln
        290                 295                 300

Ala Asp Gly Gln Asp Pro Glu Val Phe Glu Ile Pro Asp Leu Val
305                 310                 315                 320

Leu Glu Val Thr Met Glu His Pro Lys Tyr Glu Trp Phe Gln Glu Leu
                325                 330                 335

Gly Leu Lys Trp Tyr Ala Leu Pro Ala Val Ala Asn Met Leu Leu Glu
            340                 345                 350

Val Gly Gly Leu Glu Phe Pro Ala Cys Pro Phe Asn Gly Trp Tyr Met
        355                 360                 365

Gly Thr Glu Ile Gly Val Arg Asp Phe Cys Asp Thr Gln Arg Tyr Asn
370                 375                 380

Ile Leu Glu Glu Val Gly Arg Arg Met Gly Leu Glu Thr His Thr Leu
385                 390                 395                 400

Ala Ser Leu Trp Lys Asp Arg Ala Val Thr Glu Ile Asn Val Ala Val
                405                 410                 415

Leu His Ser Phe Gln Lys Gln Asn Val Thr Ile Met Asp His His Thr
            420                 425                 430

Ala Ser Glu Ser Phe Met Lys His Met Gln Asn Glu Tyr Arg Ala Arg
        435                 440                 445

Gly Gly Cys Pro Ala Asp Trp Ile Trp Leu Val Pro Pro Val Ser Gly
    450                 455                 460

Ser Ile Thr Pro Val Phe His Gln Glu Met Leu Asn Tyr Val Leu Ser
465                 470                 475                 480

Pro Phe Tyr Tyr Tyr Gln Ile Glu Pro Trp Lys Thr His Ile Trp Gln
                485                 490                 495

Asn Glu Lys Leu Arg Pro Arg Arg Glu Ile Arg Phe Arg Val Leu
            500                 505                 510

Val Lys Val Val Phe Phe Ala Ser Met Leu Met Arg Lys Val Met Ala
        515                 520                 525

Ser Arg Val Arg Ala Thr Val Leu Phe Ala Thr Glu Thr Gly Lys Ser
    530                 535                 540

Glu Ala Leu Ala Arg Asp Leu Ala Thr Leu Phe Ser Tyr Ala Phe Asn
545                 550                 555                 560

Thr Lys Val Val Cys Met Asp Gln Tyr Lys Ala Ser Thr Leu Glu Glu
                565                 570                 575

Glu Gln Leu Leu Leu Val Val Thr Ser Thr Phe Gly Asn Gly Asp Cys
            580                 585                 590

Pro Ser Asn Gly Gln Thr Leu Lys Lys Ser Leu Phe Met Leu Arg Glu
        595                 600                 605

Leu Asn His Thr Phe Arg Tyr Ala Val Phe Gly Leu Gly Ser Ser Met
    610                 615                 620
```

```
Tyr Pro Gln Phe Cys Ala Phe Ala His Asp Ile Asp Gln Lys Leu Ser
625                 630                 635                 640

His Leu Gly Ala Ser Gln Leu Ala Pro Thr Gly Glu Gly Asp Glu Leu
            645                 650                 655

Ser Gly Gln Glu Asp Ala Phe Arg Ser Trp Ala Val Gln Thr Phe Arg
                660                 665                 670

Ala Ala Cys Glu Thr Phe Asp Val Arg Ser Lys His His Ile Gln Ile
            675                 680                 685

Pro Lys Arg Phe Thr Ser Asn Ala Thr Trp Glu Pro Gln Gln Tyr Arg
690                 695                 700

Leu Ile Gln Ser Pro Glu Pro Leu Asp Leu Asn Arg Ala Leu Ser Ser
705                 710                 715                 720

Ile His Ala Lys Asn Val Phe Thr Met Arg Leu Lys Ser Gln Gln Asn
                725                 730                 735

Leu Gln Ser Glu Lys Ser Ser Arg Thr Thr Leu Leu Val Gln Leu Thr
                740                 745                 750

Phe Glu Gly Ser Arg Gly Pro Ser Tyr Leu Pro Gly Glu His Leu Gly
            755                 760                 765

Ile Phe Pro Gly Asn Gln Thr Ala Leu Val Gln Gly Ile Leu Glu Arg
770                 775                 780

Val Val Asp Cys Pro Thr Pro His Gln Thr Val Cys Leu Glu Val Leu
785                 790                 795                 800

Asp Glu Ser Gly Ser Tyr Trp Val Lys Asp Lys Arg Leu Pro Pro Cys
                805                 810                 815

Ser Leu Ser Gln Ala Leu Thr Tyr Phe Leu Asp Ile Thr Thr Pro Pro
                820                 825                 830

Thr Gln Leu Gln Leu His Lys Leu Ala Arg Phe Ala Thr Asp Glu Thr
                835                 840                 845

Asp Arg Gln Arg Leu Glu Ala Leu Cys Gln Pro Ser Glu Tyr Asn Asp
                850                 855                 860

Trp Lys Phe Ser Asn Asn Pro Thr Phe Leu Glu Val Leu Glu Glu Phe
865                 870                 875                 880

Pro Ser Leu His Val Pro Ala Ala Phe Leu Leu Ser Gln Leu Pro Ile
                885                 890                 895

Leu Lys Pro Arg Tyr Tyr Ser Ile Ser Ser Ser Gln Asp His Thr Pro
                900                 905                 910

Ser Glu Val His Leu Thr Val Ala Val Val Thr Tyr Arg Thr Arg Asp
                915                 920                 925

Gly Gln Gly Pro Leu His His Gly Val Cys Ser Thr Trp Ile Arg Asn
930                 935                 940

Leu Lys Pro Gln Asp Pro Val Pro Cys Phe Val Arg Ser Val Ser Gly
945                 950                 955                 960

Phe Gln Leu Pro Glu Asp Pro Ser Gln Pro Cys Ile Leu Ile Gly Pro
                965                 970                 975

Gly Thr Gly Ile Ala Pro Phe Arg Ser Phe Trp Gln Gln Arg Leu His
            980                 985                 990

Asp Ser Gln His Lys Gly Leu Lys Gly Gly Arg Met Ser Leu Val Phe
                995                 1000                1005

Gly Cys Arg His Pro Glu Glu Asp His Leu Tyr Gln Glu Glu Met Gln
1010                1015                1020

Glu Met Val Arg Lys Arg Val Leu Phe Gln Val His Thr Gly Tyr Ser
1025                1030                1035                1040
```

```
Arg Leu Pro Gly Lys Pro Lys Val Tyr Val Gln Asp Ile Val Gln Lys
            1045                1050                1055

Gln Leu Ala Asn Glu Val Leu Ser Val Leu His Gly Glu Gln Gly His
        1060                1065                1070

Leu Tyr Ile Cys Gly Asp Val Arg Met Ala Arg Asp Val Ala Thr Thr
        1075                1080                1085

Leu Lys Lys Leu Val Ala Thr Lys Leu Asn Leu Ser Glu Glu Gln Val
    1090                1095                1100

Glu Asp Tyr Phe Phe Gln Leu Lys Ser Gln Lys Arg Tyr His Glu Asp
1105                1110                1115                1120

Ile Phe Gly Ala Val Phe Ser Tyr Gly Ala Lys Lys Gly Ser Ala Leu
            1125                1130                1135

Glu Glu Pro Lys Ala Thr Arg Leu
            1140

<210> SEQ ID NO 3
<211> LENGTH: 4780
<212> TYPE: DNA
<213> ORGANISM: Homo sapiens

<400> SEQUENCE: 3
gagcggacgg gctcatgatg cctcagatct gatccgcatc taacaggctg gcaatgaaga      60
tacccagaga atagttcaca tctatcatgc gtcacttcta gacacagcca tcagacgcat     120
ctcctcccct ttctgcctga ccttaggaca cgtcccaccg cctctcttga cgtctgcctg     180
gtcaaccatc acttccttag agaataagga gagaggcgga tgcaggaaat catgccaccg     240
acgggccacc agccatgagt gggtgacgct gagctgacgt caaagacaga gagggctgaa     300
gccttgtcag cacctgtcac cccggctcct gctctccgtg tagcctgaag cctggatcct     360
cctggtgaaa tcatcttggc ctgatagcat tgtgaggtct tcagacagga ccctcggaa      420 gctagttacc atggaggatc acatgttcgg tgttcagcaa atccagccca atgtcatttc     480
tgttcgtctc ttcaagcgca aagttggggg cctgggattt ctggtgaagg agcgggtcag     540
taagccgccc gtgatcatct ctgacctgat tcgtgggggc gccgcagagc agagtggcct     600
catccaggcc ggagacatca ttcttgcggt caacggccgg cccttggtgg acctgagcta     660
tgacagcgcc ctggaggtac tcagaggcat tgcctctgag acccacgtgg tcctcattct     720
gaggggccct gaaggtttca ccacgcacct ggagaccacc tttacaggtg atgggacccc     780
caagaccatc cgggtgacac agccccttggg tccccccacc aaagccgtgg atctgtccca     840
ccagccaccg gccggcaaag aacagcccct ggcagtggat ggggcctcgg gtcccgggaa     900
tgggcctcag catgcctacg atgatgggca ggaggctggc tcactccccc atgccaacgg     960 ctggcccag gccccaggc aggaccccgc gaagaaagca accagagtca gcctccaagg    1020 cagagggag aacaatgaac tgctcaagga gatagagcct gtgctgagcc ttctcaccag    1080
tgggagcaga ggggtcaagg gaggggcacc tgccaaggca gagatgaaag atatgggaat    1140
ccaggtggac agagatttgg acggcaagtc acacaaacct ctgcccctcg cgtggagaa    1200 cgaccgagtc ttcaatgacc tatggggggaa gggcaatgtg cctgtcgtcc tcaacaaccc    1260
atattcagag aaggagcagc cccccacctc aggaaaacag tccccacaa agaatggcag    1320 cccctccaag tgtccacgct cctcaaggt caagaactgg gagactgagg tggttctcac    1380 tgacacccctc cacctaaga gcacattgga acgggatgc actgagtaca tctgcatggg    1440
ctccatcatg catccttctc agcatgcaag gaggcctgaa gacgtccgca caaaaggaca    1500
```

-continued

```
gctcttccct ctcgccaaag agtttattga tcaatactat tcatcaatta aaagatttgg    1560
ctccaaagcc cacatggaaa ggctggaaga ggtgaacaaa gagatcgaca ccactagcac    1620
ttaccagctc aaggacacag agctcatcta tggggccaag cacgcctggc ggaatgcctc    1680
gcgctgtgtg ggcaggatcc agtggtccaa gctgcaggta ttcgatgccc gtgactgcac    1740
cacggcccac gggatgttca actacatctg taaccatgtc aagtatgcca ccaacaaagg    1800
gaacctcagg tctgccatca ccatattccc ccagaggaca gacggcaagc acgacttccg    1860
agtctggaac tcccagctca tccgctacgc tggctacaag caccgtgacg gctccaccct    1920
gggggaccca gccaatgtgc agttcacaga gatatgcata cagcagggct ggaaaccgcc    1980
tagaggccgc ttcgatgtcc tgccgctcct gcttcaggcc aacggcaatg accctgagct    2040
cttccagatt cctccagagc tggtgttgga acttcccatc aggcacccca gtttgagtg     2100 gttcaaggac ctggcgctga agtggtacgg cctccccgcc gtgtccaaca tgctcctaga    2160
gattggcggc ctggagttca gcgcctgtcc cttcagtggc tggtacatgg gcacagagat    2220
tggtgtccgc gactactgtg caactcccg ctacaatatc ctggaggaag tggccaagaa     2280
gatgaactta gacatgagga agacgtcctc cctgtggaag gaccaggcgc tggtggagat    2340
caatatcgcg gttctctata gcttccagag tgacaaagtg accattgttg accatcactc    2400
cgccaccgag tccttcatta agcacatgga gaatgagtac cgctgccggg ggggctgccc    2460
tgccgactgg gtgtggatcg tgcccccca gtccggaagc atcacccctg tgttccacca    2520
ggagatgctc aactaccggc tcacccccc cttcgaatac cagcctgatc cctggaacac     2580
gcatgtctgg aaaggcacca acgggacccc cacaaagcgg cgagccatcg gcttcaagaa    2640
gctagcagaa gctgtcaagt tctcggccaa gctgatgggg caggctatgg ccaagagggt    2700
gaaagcgacc atcctctatg ccacagagac aggcaaatcg caagcttatg ccaagacctt    2760
gtgtgagatc ttcaaacacg cctttgatgc caaggtgatg tccatggaag aatatgacat    2820
tgtgcacctg gaacatgaaa ctctggtcct tgtggtcacc agcacctttg caatggaga    2880 tcccctgag aatggggaga aattcggctg tgctttgatg gaaatgaggc accccaactc     2940
tgtgcaggaa gaaaggaaga gctacaaggt ccgattcaac agcgtctcct cctactctga    3000
ctcccaaaaa tcatcaggcg atgggcccga cctcagagac aactttgaga gtgctggacc    3060
cctggccaat gtgaggttct cagttttttgg cctcggctca cgagcatacc ctcactttttg    3120 cgccttcgga cacgctgtgg acaccctcct ggaagaactg ggaggggaga ggatcctgaa    3180
gatgagggaa ggggatgagc tctgtgggca ggaagaggct ttcaggacct gggccaagaa    3240
ggtcttcaag gcagcctgtg atgtcttctg tgtgggagat gatgtcaaca ttgaaaaggc    3300
caacaattcc ctcatcagca atgatcgcag ctggaagaga aacaagttcc gcctcacctt    3360
tgtggccgaa gctccagaac tcacacaagg tctatccaat gtccacaaaa agcgagtctc    3420
agctgcccgg ctccttagcc gtcaaaacct ccagagccct aaatccagtc ggtcaactat    3480
cttcgtgcgt ctccacacca acgggagcca ggagctgcag taccagcctg ggaccacct    3540 gggtgtcttc cctggcaacc acgaggacct cgtgaatgcc ctgatcgagc ggctggagga    3600
cgcgccgcct gtcaaccaga tggtgaaagt ggaactgctg gaggagcgga cacggctttt    3660
aggtgtcatc agtaactgga cagacgagct ccgcctcccg ccctgcacca tcttccaggc    3720
cttcaagtac tacctggaca tcaccacgcc accaacgcct ctgcagctgc agcagtttgc    3780
ctccctagct accagcgaga aggagaagca gcgtctgctg gtcctcagca agggtttgca    3840
ggagtacgag gaatggaaat ggggcaagaa cccccaccatc gtggaggtgc tggaggagtt    3900
```

```
cccatctatc cagatgccgg ccaccctgct cctgacccag ctgtccctgc tgcagccccg    3960
ctactattcc atcagctcct ccccagacat gtaccctgat gaagtgcacc tcactgtggc    4020
catcgtttcc taccgcactc gagatggaga aggaccaatt caccacggcg tatgctcctc    4080
ctggctcaac cggatacagg ctgacgaact ggtcccctgt ttcgtgagag gagcacccag    4140
cttccacctg ccccggaacc cccaagtccc ctgcatcctc gttggaccag gcaccggcat    4200 tgccccttc cgaagcttct ggcaacagcg gcaatttgat atccaacaca aggaatgaa     4260 cccctgcccc atggtcctgg tcttcgggtg ccggcaatcc aagatagatc atatctacag    4320
ggaagagacc ctgcaggcca agaacaaggg ggtcttcaga gagctgtaca cggcttactc    4380
ccgggagcca gacaaaccaa agaagtacgt gcaggacatc ctgcaggagc agctggcgga    4440
gtctgtgtac cgagccctga aggagcaagg gggccacata tacgtctgtg gggacgtcac    4500
catggctgct gatgtcctca aagccatcca gcgcatcatg acccagcagg gaagctctc    4560 ggcagaggac gccggcgtat tcatcagccg gatgagggat gacaaccgat accatgagga    4620 tattttgga gtcaccctgc gaacgatcga agtgaccaac cgccttagat ctgagtccat    4680
tgccttcatt gaagagagca aaaaagacac cgatgaggtt ttcagctcct aactggaccc    4740
tcttgcccag ccggctgcaa gtttgtaagc gcgggacaga                         4780
```

<210> SEQ ID NO 4
<211> LENGTH: 1433
<212> TYPE: PRT
<213> ORGANISM: Homo sapiens

<400> SEQUENCE: 4

```
Met Glu Asp His Met Phe Gly Val Gln Gln Ile Gln Pro Asn Val Ile
 1               5                  10                  15

Ser Val Arg Leu Phe Lys Arg Lys Val Gly Gly Leu Gly Phe Leu Val
            20                  25                  30

Lys Glu Arg Val Ser Lys Pro Pro Val Ile Ile Ser Asp Leu Ile Arg
        35                  40                  45

Gly Gly Ala Ala Glu Gln Ser Gly Leu Ile Gln Ala Gly Asp Ile Ile
    50                  55                  60

Leu Ala Val Asn Gly Arg Pro Leu Val Asp Leu Ser Tyr Asp Ser Ala
65                  70                  75                  80

Leu Glu Val Leu Arg Gly Ile Ala Ser Glu Thr His Val Val Leu Ile
                85                  90                  95

Leu Arg Gly Pro Glu Gly Phe Thr Thr His Leu Glu Thr Thr Phe Thr
            100                 105                 110

Gly Asp Gly Thr Pro Lys Thr Ile Arg Val Thr Gln Pro Leu Gly Pro
        115                 120                 125

Pro Thr Lys Ala Val Asp Leu Ser His Gln Pro Pro Ala Gly Lys Glu
    130                 135                 140

Gln Pro Leu Ala Val Asp Gly Ala Ser Gly Pro Gly Asn Gly Pro Gln
145                 150                 155                 160

His Ala Tyr Asp Asp Gly Gln Glu Ala Gly Ser Leu Pro His Ala Asn
                165                 170                 175

Gly Trp Pro Gln Ala Pro Arg Gln Asp Pro Ala Lys Lys Ala Thr Arg
            180                 185                 190

Val Ser Leu Gln Gly Arg Gly Glu Asn Asn Glu Leu Leu Lys Glu Ile
        195                 200                 205

Glu Pro Val Leu Ser Leu Leu Thr Ser Gly Ser Arg Gly Val Lys Gly
```

-continued

```
            210                 215                 220
Gly Ala Pro Ala Lys Ala Glu Met Lys Asp Met Gly Ile Gln Val Asp
225                 230                 235                 240

Arg Asp Leu Asp Gly Lys Ser His Lys Pro Leu Pro Leu Gly Val Glu
                245                 250                 255

Asn Asp Arg Val Phe Asn Asp Leu Trp Gly Lys Gly Asn Val Pro Val
            260                 265                 270

Val Leu Asn Asn Pro Tyr Ser Glu Lys Glu Gln Pro Thr Ser Gly
            275                 280                 285

Lys Gln Ser Pro Thr Lys Asn Gly Ser Pro Ser Lys Cys Pro Arg Phe
290                 295                 300

Leu Lys Val Lys Asn Trp Glu Thr Glu Val Val Leu Thr Asp Thr Leu
305                 310                 315                 320

His Leu Lys Ser Thr Leu Glu Thr Gly Cys Thr Glu Tyr Ile Cys Met
                325                 330                 335

Gly Ser Ile Met His Pro Ser Gln His Ala Arg Arg Pro Glu Asp Val
            340                 345                 350

Arg Thr Lys Gly Gln Leu Phe Pro Leu Ala Lys Glu Phe Ile Asp Gln
                355                 360                 365

Tyr Tyr Ser Ser Ile Lys Arg Phe Gly Ser Lys Ala His Met Glu Arg
370                 375                 380

Leu Glu Glu Val Asn Lys Glu Ile Asp Thr Thr Ser Thr Tyr Gln Leu
385                 390                 395                 400

Lys Asp Thr Glu Leu Ile Tyr Gly Ala Lys His Ala Trp Arg Asn Ala
                405                 410                 415

Ser Arg Cys Val Gly Arg Ile Gln Trp Ser Lys Leu Gln Val Phe Asp
                420                 425                 430

Ala Arg Asp Cys Thr Thr Ala His Gly Met Phe Asn Tyr Ile Cys Asn
                435                 440                 445

His Val Lys Tyr Ala Thr Asn Lys Gly Asn Leu Arg Ser Ala Ile Thr
            450                 455                 460

Ile Phe Pro Gln Arg Thr Asp Gly Lys His Asp Phe Arg Val Trp Asn
465                 470                 475                 480

Ser Gln Leu Ile Arg Tyr Ala Gly Tyr Lys His Arg Asp Gly Ser Thr
                485                 490                 495

Leu Gly Asp Pro Ala Asn Val Gln Phe Thr Glu Ile Cys Ile Gln Gln
                500                 505                 510

Gly Trp Lys Pro Pro Arg Gly Arg Phe Asp Val Leu Pro Leu Leu Leu
            515                 520                 525

Gln Ala Asn Gly Asn Asp Pro Glu Leu Phe Gln Ile Pro Pro Glu Leu
            530                 535                 540

Val Leu Glu Leu Pro Ile Arg His Pro Lys Phe Glu Trp Phe Lys Asp
545                 550                 555                 560

Leu Ala Leu Lys Trp Tyr Gly Leu Pro Ala Val Ser Asn Met Leu Leu
                565                 570                 575

Glu Ile Gly Gly Leu Glu Phe Ser Ala Cys Pro Phe Ser Gly Trp Tyr
            580                 585                 590

Met Gly Thr Glu Ile Gly Val Arg Asp Tyr Cys Asp Asn Ser Arg Tyr
            595                 600                 605

Asn Ile Leu Glu Glu Val Ala Lys Lys Met Asn Leu Asp Met Arg Lys
            610                 615                 620

Thr Ser Ser Leu Trp Lys Asp Gln Ala Leu Val Glu Ile Asn Ile Ala
625                 630                 635                 640
```

-continued

```
Val Leu Tyr Ser Phe Gln Ser Asp Lys Val Thr Ile Val Asp His His
            645                 650                 655
Ser Ala Thr Glu Ser Phe Ile Lys His Met Glu Asn Glu Tyr Arg Cys
            660                 665                 670
Arg Gly Gly Cys Pro Ala Asp Trp Val Trp Ile Val Pro Pro Met Ser
            675                 680                 685
Gly Ser Ile Thr Pro Val Phe His Gln Glu Met Leu Asn Tyr Arg Leu
            690                 695                 700
Thr Pro Ser Phe Glu Tyr Gln Pro Asp Pro Trp Asn Thr His Val Trp
705                 710                 715                 720
Lys Gly Thr Asn Gly Thr Pro Thr Lys Arg Arg Ala Ile Gly Phe Lys
            725                 730                 735
Lys Leu Ala Glu Ala Val Lys Phe Ser Ala Lys Leu Met Gly Gln Ala
            740                 745                 750
Met Ala Lys Arg Val Lys Ala Thr Ile Leu Tyr Ala Thr Glu Thr Gly
            755                 760                 765
Lys Ser Gln Ala Tyr Ala Lys Thr Leu Cys Glu Ile Phe Lys His Ala
            770                 775                 780
Phe Asp Ala Lys Val Met Ser Met Glu Glu Tyr Asp Ile Val His Leu
785                 790                 795                 800
Glu His Glu Thr Leu Val Leu Val Thr Ser Thr Phe Gly Asn Gly
            805                 810                 815
Asp Pro Pro Glu Asn Gly Glu Lys Phe Gly Cys Ala Leu Met Glu Met
            820                 825                 830
Arg His Pro Asn Ser Val Gln Glu Glu Arg Lys Ser Tyr Lys Val Arg
            835                 840                 845
Phe Asn Ser Val Ser Ser Tyr Ser Asp Ser Gln Lys Ser Ser Gly Asp
            850                 855                 860
Gly Pro Asp Leu Arg Asp Asn Phe Glu Ser Ala Gly Pro Leu Ala Asn
865                 870                 875                 880
Val Arg Phe Ser Val Phe Gly Leu Gly Ser Arg Ala Tyr Pro His Phe
            885                 890                 895
Cys Ala Phe Gly His Ala Val Asp Thr Leu Leu Glu Glu Leu Gly Gly
            900                 905                 910
Glu Arg Ile Leu Lys Met Arg Glu Gly Asp Glu Leu Cys Gly Gln Glu
            915                 920                 925
Glu Ala Phe Arg Thr Trp Ala Lys Lys Val Phe Lys Ala Ala Cys Asp
            930                 935                 940
Val Phe Cys Val Gly Asp Asp Val Asn Ile Glu Lys Ala Asn Asn Ser
945                 950                 955                 960
Leu Ile Ser Asn Asp Arg Ser Trp Lys Arg Asn Lys Phe Arg Leu Thr
            965                 970                 975
Phe Val Ala Glu Ala Pro Glu Leu Thr Gln Gly Leu Ser Asn Val His
            980                 985                 990
Lys Lys Arg Val Ser Ala Ala Arg Leu Leu Ser Arg Gln Asn Leu Gln
            995                1000                1005
Ser Pro Lys Ser Ser Arg Ser Thr Ile Phe Val Arg Leu His Thr Asn
       1010                1015                1020
Gly Ser Gln Glu Leu Gln Tyr Gln Pro Gly Asp His Leu Gly Val Phe
       1025                1030                1035                1040
Pro Gly Asn His Glu Asp Leu Val Asn Ala Leu Ile Glu Arg Leu Glu
                  1045                1050                1055
```

-continued

Asp Ala Pro Pro Val Asn Gln Met Val Lys Val Glu Leu Leu Glu Glu
                1060                1065                1070

Arg Asn Thr Ala Leu Gly Val Ile Ser Asn Trp Thr Asp Glu Leu Arg
        1075                1080                1085

Leu Pro Pro Cys Thr Ile Phe Gln Ala Phe Lys Tyr Tyr Leu Asp Ile
    1090                1095                1100

Thr Thr Pro Pro Thr Pro Leu Gln Leu Gln Gln Phe Ala Ser Leu Ala
1105                1110                1115                1120

Thr Ser Glu Lys Glu Lys Gln Arg Leu Leu Val Leu Ser Lys Gly Leu
                1125                1130                1135

Gln Glu Tyr Glu Glu Trp Lys Trp Gly Lys Asn Pro Thr Ile Val Glu
        1140                1145                1150

Val Leu Glu Glu Phe Pro Ser Ile Gln Met Pro Ala Thr Leu Leu Leu
    1155                1160                1165

Thr Gln Leu Ser Leu Leu Gln Pro Arg Tyr Tyr Ser Ile Ser Ser Ser
1170                1175                1180

Pro Asp Met Tyr Pro Asp Glu Val His Leu Thr Val Ala Ile Val Ser
1185                1190                1195                1200

Tyr Arg Thr Arg Asp Gly Glu Gly Pro Ile His His Gly Val Cys Ser
                1205                1210                1215

Ser Trp Leu Asn Arg Ile Gln Ala Asp Glu Leu Val Pro Cys Phe Val
        1220                1225                1230

Arg Gly Ala Pro Ser Phe His Leu Pro Arg Asn Pro Gln Val Pro Cys
    1235                1240                1245

Ile Leu Val Gly Pro Gly Thr Gly Ile Ala Pro Phe Arg Ser Phe Trp
1250                1255                1260

Gln Gln Arg Gln Phe Asp Ile Gln His Lys Gly Met Asn Pro Cys Pro
1265                1270                1275                1280

Met Val Leu Val Phe Gly Cys Arg Gln Ser Lys Ile Asp His Ile Tyr
                1285                1290                1295

Arg Glu Glu Thr Leu Gln Ala Lys Asn Lys Gly Val Phe Arg Glu Leu
        1300                1305                1310

Tyr Thr Ala Tyr Ser Arg Glu Pro Asp Lys Pro Lys Lys Tyr Val Gln
    1315                1320                1325

Asp Ile Leu Gln Glu Gln Leu Ala Glu Ser Val Tyr Arg Ala Leu Lys
1330                1335                1340

Glu Gln Gly Gly His Ile Tyr Val Cys Gly Asp Val Thr Met Ala Ala
1345                1350                1355                1360

Asp Val Leu Lys Ala Ile Gln Arg Ile Met Thr Gln Gln Gly Lys Leu
                1365                1370                1375

Ser Ala Glu Asp Ala Gly Val Phe Ile Ser Arg Met Arg Asp Asp Asn
        1380                1385                1390

Arg Tyr His Glu Asp Ile Phe Gly Val Thr Leu Arg Thr Ile Glu Val
    1395                1400                1405

Thr Asn Arg Leu Arg Ser Glu Ser Ile Ala Phe Ile Glu Glu Ser Lys
1410                1415                1420

Lys Asp Thr Asp Glu Val Phe Ser Ser
1425                1430

<210> SEQ ID NO 5
<211> LENGTH: 4097
<212> TYPE: DNA
<213> ORGANISM: Bos taurus

<400> SEQUENCE: 5

```
gaattcggca cgaggagcca cagagcagac ggaggccgcc cgtccggccc cagcgacatg      60
ggcaacttga agagtgtggg ccaggagccc gggcccccct gcggcctggg gctggggctg     120
ggcctcgggc tatgcggcaa gcagggccca gcctccccgg cacctgagcc cagccgggcc     180
cccgcacccg ccaccccgca cgcgccagac acagcccag ctcccaacag ccccacgctg      240
acccggcctc cggaggggcc caagttccct cgcgtgaaga actgggagct ggggagcatc     300
acctacgaca ctctgtgcgc gcagtcccaa caggacgggc cctgcactcc caggcgctgc     360
ctgggctccc tggtgttgcc ccggaaactg cagacccggc cctccccggg acctccaccc     420
gctgagcagc tgctgagcca ggccagggac ttcatcaacc agtactacag ctccatcaag     480
aggagcggct cccaggctca cgaggagcgg cttcaggagg tggaggccga ggtggcatcc     540
acgggcacca tccacctccg agagagtgag ctggtgttcg ggccaagca ggcctggcgc       600 aatgcacccc gctgcgtggg ccgcatccag tgggggaagc tgcaggtgtt tgatgcccgg     660
gactgcagct cagcacagga gatgttcacc tacatctgca accacatcaa gtacgccacc     720
aaccgcggca accttcgctc ggccatcaca gtgttcccgc agcgcgcccc gggccgcgga     780
gacttccgga tctggaacag ccagctggtg cgctacgcag gctacagaca gcaggatggc     840
tctgtgcgtg gggacccagc caacgtggag atcacggagc tctgcatcca gcacggctgg     900 accccccggaa acggccgctt cgacgtgctg ccccctgctgc tccaggcccc agacgaggct   960
ccagagctct ttgttctgcc ccccgagctg gtccttgaag tgcccctagg agcaccccac    1020
actggagtgg ttcgcggccc tgggctgcga tggtatgccc tcccggccgt gtccaacatg    1080
ctgctggaaa tcgggggtct ggagttctcc gcggcccccct tcagcggctg gtacatgagc    1140
acggagattg gcacgcggaa cctgtgtgac cctcaccgct acaatatcct ggaggatgtg    1200
gccgtctgca tggacctcga cacgcggacc acctcgtccc tgtggaagga caaggcggcc    1260
gtggagatca acctggctgt gctgcacagc tttcagctcg ccaaggtgac catcgtggac    1320
caccacgccg ccacggtgtc cttcatgaag cacctggaca cgagcagaa ggccaggggg     1380 ggctgccccg ccgactgggc ctggatcgtg cccccatct acggcagcct accgcccgtc     1440
ttccaccagg agatggtcaa ctacatcctg tccctgcct tccgctacca gccagacccc     1500
tggaaaggga gcgcgaccaa gggcgccggc atcaccagga agaagacctt taaggaagtg    1560
gccaacgcgg tgaagatctc tgcctcactc atgggcaccc tgatggccaa gcgagtgaaa    1620
gcaaccatcc tgtacgcctc tgagaccggc cgggcccaga gctacgctca gcagctgggg    1680
aggctcttcc ggaaggcctt cgatccccgg gtcctgtgca tggatgagta tgacgtggtg    1740
tccctggagc acgaggcact ggtgctgtg gtgaccagca cctttgggaa tggcgatccc    1800
ccggagaatg gagagagttt tgcagctgcc ctgatggaga tgtcggggcc ctacaacagc    1860
tccccacggc cggaacagca caagagttac aagatccgct tcaacagcgt ctcctgctca    1920
gacccgctgg tgtcctcctg gcggcggaag agaaaggagt ccagcaacac agacagcgcg    1980
ggggccctgg ggaccctcag gttctgtgtg ttcggactgg gctcccggc gtaccccac      2040 ttctgcgcct tcgcgcgagc ggtggacacc cggctggaag agcttggagg ggagcggctg    2100
ctgcagctgg gccaggcgga tgagctctgc ggccaggaag aggccttccg tggttgggca    2160
aaggcggcat tccaggcctc ctgcgagacg ttctgcgttg gggaggaggc caaggctgct    2220
gcccaggaca tcttcagccc caaacggagc tggaaacgcc agaggtaccg gctgagcgcc    2280
caggccgagg gcctccagct gctgccaggc ctgatccacg tgcacagacg gaagatgttt    2340
```

-continued

```
caggccacag tcctctcggt ggaaaatctg caaagcagca agtccacccg ggccaccatc    2400
ctggtgcgcc tggacactgc aggccaggag gggctgcagt accagccggg ggaccacata    2460
ggcatctccg cgcccaaccg gccgggcctg gtggaggcgc tgctgagccg cgtggaggac    2520
ccgccaccgc ccaccgagtc tgtggctgtg gagcagctgg agaaaggcag cccaggcggc    2580
cctcctccca gctgggtgcg ggacccacgg ctgcccccgt gcaccgtgcg ccaggctctc    2640
accttcttcc tggacatcac ctccccaccc agccccggc ttctccgact gctcagcacc     2700
ctggccgaag aacccagcga gcagcaggag cttgagaccc tcagtcagga ccccggcgc    2760 tacgaggagt ggaagttggt ccgctgcccc acgctgctgg aggtgctgga gcagttcccg    2820
tccgtggcgc tgcccgcccc gctgctcctc acccagctgc cctgctgca gccccggtac    2880 tactctgtca gctcggcccc caacgcccac cccggagagg tccacctcac agtggccgtg    2940
ctggcgtaca ggacccaaga tgggctgggc cccctacact acgggtctg ctccacatgg     3000 ctgagccagc tcaagactgg agaccccgtg ccctgcttca tcaggggggc tccctccttc    3060
cggctgccgc ctgaccccta cgtgccctgc atcctcgtgg gccctggcac tggcatcgcc    3120
cccttccggg gattttggca ggagaggctg catgacattg agagcaaagg gctgcagccg    3180 cacccccatga ccctggtgtt cggctgccgc tgctcccaac tcgaccatct ctaccgcgac    3240
gaggtgcagg acgcccagga gcgcgggtg tttggccgcg tcctcaccgc cttctcccgg     3300
gaacctgaca gccccaagac ctacgtacag gacatcctga gaaccgagct ggctgccgag    3360
gtgcaccgcg tgctgtgcct cgagcggggc cacatgtttg tctgcggcga tgtcactatg    3420
gcaaccagcg tcctgcagac ggtgcagcgc atcttggcga cagagggcga catggagctg    3480
gacgaggcgg gcgacgtcat cggcgtgctg cgggatcagc aacgctatca cgaggacatt    3540
ttcggcctca cgctgcgcac ccaggaggtg acaagccgta tacgtaccca gagcttttcc    3600
ctgcaggagc ggcatctgcg gggcgcggtg ccctgggcct cgacccgcc cggcccagac    3660 acccccggcc cctgagaccc ctcttgcttc ccactgcagt tcccggagag agggggctgtc    3720 attccactat ggctctaccg ctgtcctgtt ggcctttacc gggaccggcc acctctccct    3780
cccctcccaa ggtgacttcc cagagactgt tggattccct gtactatctc atcctctcat    3840
ctctaggtct gtttccccac cctaagtcca tctggaagac ccctcccagc agcggtattc    3900
cagagcctac agtcagccct ttggtgttta ggtgaatttt agattcccct cgcctctctc    3960
ccgggaagta tcttatcttg aaacctgatc tctaaatcat tcaaatattt attattgaag    4020
atttaccata agagactgga ccagaagtta ggagacctac taagatgcct aagccaaggt    4080
cctccggggc cgaattc                                                   4097
```

<210> SEQ ID NO 6
<211> LENGTH: 1205
<212> TYPE: PRT
<213> ORGANISM: Bos taurus

<400> SEQUENCE: 6

```
Met Gly Asn Leu Lys Ser Val Gly Gln Glu Pro Gly Pro Pro Cys Gly
  1               5                  10                  15

Leu Gly Leu Gly Leu Gly Leu Gly Leu Cys Lys Gln Gly Pro Ala
             20                  25                  30

Ser Pro Ala Pro Glu Pro Ser Arg Ala Pro Ala Pro Thr Pro His
         35                  40                  45

Ala Pro Asp His Ser Pro Ala Pro Asn Ser Pro Thr Leu Thr Arg Pro
     50                  55                  60
```

-continued

```
Pro Glu Gly Pro Lys Phe Pro Arg Val Lys Asn Trp Glu Leu Gly Ser
 65                  70                  75                  80

Ile Thr Tyr Asp Thr Leu Cys Ala Gln Ser Gln Gln Asp Gly Pro Cys
                 85                  90                  95

Thr Pro Arg Arg Cys Leu Gly Ser Leu Val Leu Pro Arg Lys Leu Gln
            100                 105                 110

Thr Arg Pro Ser Pro Gly Pro Pro Ala Glu Gln Leu Leu Ser Gln
            115                 120                 125

Ala Arg Asp Phe Ile Asn Gln Tyr Tyr Ser Ser Ile Lys Arg Ser Gly
    130                 135                 140

Ser Gln Ala His Glu Glu Arg Leu Gln Glu Val Glu Ala Glu Val Ala
145                 150                 155                 160

Ser Thr Gly Thr Ile His Leu Arg Glu Ser Glu Leu Val Phe Gly Ala
                165                 170                 175

Lys Gln Ala Trp Arg Asn Ala Pro Arg Cys Val Gly Arg Ile Gln Trp
            180                 185                 190

Gly Lys Leu Gln Val Phe Asp Ala Arg Asp Cys Ser Ser Ala Gln Glu
            195                 200                 205

Met Phe Thr Tyr Ile Cys Asn His Ile Lys Tyr Ala Thr Asn Arg Gly
    210                 215                 220

Asn Leu Arg Ser Ala Ile Thr Val Phe Pro Gln Arg Ala Pro Gly Arg
225                 230                 235                 240

Gly Asp Phe Arg Ile Trp Asn Ser Gln Leu Val Arg Tyr Ala Gly Tyr
                245                 250                 255

Arg Gln Gln Asp Gly Ser Val Arg Gly Asp Pro Ala Asn Val Glu Ile
            260                 265                 270

Thr Glu Leu Cys Ile Gln His Gly Trp Thr Pro Gly Asn Gly Arg Phe
            275                 280                 285

Asp Val Leu Pro Leu Leu Leu Gln Ala Pro Asp Glu Ala Pro Glu Leu
    290                 295                 300

Phe Val Leu Pro Pro Glu Leu Val Leu Glu Val Pro Leu Gly Ala Pro
305                 310                 315                 320

His Thr Gly Val Val Arg Gly Pro Gly Leu Arg Trp Tyr Ala Leu Pro
                325                 330                 335

Ala Val Ser Asn Met Leu Leu Glu Ile Gly Gly Leu Glu Phe Ser Ala
            340                 345                 350

Ala Pro Phe Ser Gly Trp Tyr Met Ser Thr Glu Ile Gly Thr Arg Asn
            355                 360                 365

Leu Cys Asp Pro His Arg Tyr Asn Ile Leu Glu Asp Val Ala Val Cys
    370                 375                 380

Met Asp Leu Asp Thr Arg Thr Thr Ser Ser Leu Trp Lys Asp Lys Ala
385                 390                 395                 400

Ala Val Glu Ile Asn Leu Ala Val Leu His Ser Phe Gln Leu Ala Lys
                405                 410                 415

Val Thr Ile Val Asp His His Ala Ala Thr Val Ser Phe Met Lys His
            420                 425                 430

Leu Asp Asn Glu Gln Lys Ala Arg Gly Gly Cys Pro Ala Asp Trp Ala
            435                 440                 445

Trp Ile Val Pro Pro Ile Tyr Gly Ser Leu Pro Pro Val Phe His Gln
    450                 455                 460

Glu Met Val Asn Tyr Ile Leu Ser Pro Ala Phe Arg Tyr Gln Pro Asp
465                 470                 475                 480
```

-continued

```
Pro Trp Lys Gly Ser Ala Thr Lys Gly Ala Gly Ile Thr Arg Lys Lys
            485                 490                 495

Thr Phe Lys Glu Val Ala Asn Ala Val Lys Ile Ser Ala Ser Leu Met
            500                 505                 510

Gly Thr Leu Met Ala Lys Arg Val Lys Ala Thr Ile Leu Tyr Ala Ser
            515                 520                 525

Glu Thr Gly Arg Ala Gln Ser Tyr Ala Gln Gln Leu Gly Arg Leu Phe
            530                 535                 540

Arg Lys Ala Phe Asp Pro Arg Val Leu Cys Met Asp Glu Tyr Asp Val
545                 550                 555                 560

Val Ser Leu Glu His Glu Ala Leu Val Leu Val Thr Ser Thr Phe
            565                 570                 575

Gly Asn Gly Asp Pro Pro Glu Asn Gly Glu Ser Phe Ala Ala Ala Leu
            580                 585                 590

Met Glu Met Ser Gly Pro Tyr Asn Ser Ser Pro Arg Pro Glu Gln His
            595                 600                 605

Lys Ser Tyr Lys Ile Arg Phe Asn Ser Val Ser Cys Ser Asp Pro Leu
            610                 615                 620

Val Ser Ser Trp Arg Arg Lys Arg Lys Glu Ser Ser Asn Thr Asp Ser
625                 630                 635                 640

Ala Gly Ala Leu Gly Thr Leu Arg Phe Cys Val Phe Gly Leu Gly Ser
            645                 650                 655

Arg Ala Tyr Pro His Phe Cys Ala Phe Ala Arg Ala Val Asp Thr Arg
            660                 665                 670

Leu Glu Glu Leu Gly Gly Glu Arg Leu Leu Gln Leu Gly Gln Gly Asp
            675                 680                 685

Glu Leu Cys Gly Gln Glu Ala Phe Arg Gly Trp Ala Lys Ala Ala
            690                 695                 700

Phe Gln Ala Ser Cys Glu Thr Phe Cys Val Gly Glu Glu Ala Lys Ala
705                 710                 715                 720

Ala Ala Gln Asp Ile Phe Ser Pro Lys Arg Ser Trp Lys Arg Gln Arg
            725                 730                 735

Tyr Arg Leu Ser Ala Gln Ala Glu Gly Leu Gln Leu Leu Pro Gly Leu
            740                 745                 750

Ile His Val His Arg Arg Lys Met Phe Gln Ala Thr Val Leu Ser Val
            755                 760                 765

Glu Asn Leu Gln Ser Ser Lys Ser Thr Arg Ala Thr Ile Leu Val Arg
            770                 775                 780

Leu Asp Thr Ala Gly Gln Glu Gly Leu Gln Tyr Gln Pro Gly Asp His
785                 790                 795                 800

Ile Gly Ile Ser Ala Pro Asn Arg Pro Gly Leu Val Glu Ala Leu Leu
            805                 810                 815

Ser Arg Val Glu Asp Pro Pro Pro Thr Glu Ser Val Ala Val Glu
            820                 825                 830

Gln Leu Glu Lys Gly Ser Pro Gly Gly Pro Pro Ser Trp Val Arg
            835                 840                 845

Asp Pro Arg Leu Pro Pro Cys Thr Val Arg Gln Ala Leu Thr Phe Phe
850                 855                 860

Leu Asp Ile Thr Ser Pro Pro Ser Pro Arg Leu Leu Arg Leu Leu Ser
865                 870                 875                 880

Thr Leu Ala Glu Glu Pro Ser Glu Gln Gln Glu Leu Glu Thr Leu Ser
            885                 890                 895

Gln Asp Pro Arg Arg Tyr Glu Glu Trp Lys Leu Val Arg Cys Pro Thr
```

-continued

```
                       900                    905                    910
Leu Leu Glu Val Leu Glu Gln Phe Pro Ser Val Ala Leu Pro Ala Pro
            915                    920                  925

Leu Leu Leu Thr Gln Leu Pro Leu Leu Gln Pro Arg Tyr Tyr Ser Val
        930                    935                  940

Ser Ser Ala Pro Asn Ala His Pro Gly Glu Val His Leu Thr Val Ala
945                      950                  955                  960

Val Leu Ala Tyr Arg Thr Gln Asp Gly Leu Gly Pro Leu His Tyr Gly
                    965                  970                  975

Val Cys Ser Thr Trp Leu Ser Gln Leu Lys Thr Gly Asp Pro Val Pro
                980                  985                  990

Cys Phe Ile Arg Gly Ala Pro Ser Phe Arg Leu Pro Pro Asp Pro Tyr
            995                 1000                 1005

Val Pro Cys Ile Leu Val Gly Pro Gly Thr Gly Ile Ala Pro Phe Arg
        1010                   1015                 1020

Gly Phe Trp Gln Glu Arg Leu His Asp Ile Glu Ser Lys Gly Leu Gln
1025                    1030                 1035                 1040

Pro His Pro Met Thr Leu Val Phe Gly Cys Arg Cys Ser Gln Leu Asp
                1045                 1050                 1055

His Leu Tyr Arg Asp Glu Val Gln Asp Ala Gln Glu Arg Gly Val Phe
            1060                 1065                 1070

Gly Arg Val Leu Thr Ala Phe Ser Arg Glu Pro Asp Ser Pro Lys Thr
        1075                 1080                 1085

Tyr Val Gln Asp Ile Leu Arg Thr Glu Leu Ala Ala Glu Val His Arg
    1090                 1095                 1100

Val Leu Cys Leu Glu Arg Gly His Met Phe Val Cys Gly Asp Val Thr
1105                 1110                 1115                 1120

Met Ala Thr Ser Val Leu Gln Thr Val Gln Arg Ile Leu Ala Thr Glu
            1125                 1130                 1135

Gly Asp Met Glu Leu Asp Glu Ala Gly Asp Val Ile Gly Val Leu Arg
                1140                 1145                 1150

Asp Gln Gln Arg Tyr His Glu Asp Ile Phe Gly Leu Thr Leu Arg Thr
        1155                 1160                 1165

Gln Glu Val Thr Ser Arg Ile Arg Thr Gln Ser Phe Ser Leu Gln Glu
    1170                 1175                 1180

Arg His Leu Arg Gly Ala Val Pro Trp Ala Phe Asp Pro Pro Gly Pro
1185                 1190                 1195                 1200

Asp Thr Pro Gly Pro
                1205
```